(12) United States Patent
Maruoka et al.

(10) Patent No.: US 8,367,820 B2
(45) Date of Patent: Feb. 5, 2013

(54) OPTICALLY ACTIVE AMMONIUM SALT COMPOUND, PRODUCTION INTERMEDIATE THEREOF, AND PRODUCTION METHOD THEREOF

(75) Inventors: Keiji Maruoka, Kyoto (JP); Yasushi Kubota, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 885 days.

(21) Appl. No.: 11/817,585

(22) PCT Filed: Mar. 3, 2006

(86) PCT No.: PCT/JP2006/304091
§ 371 (c)(1),
(2), (4) Date: Sep. 25, 2009

(87) PCT Pub. No.: WO2006/093269
PCT Pub. Date: Sep. 8, 2006

(65) Prior Publication Data
US 2010/0041881 A1 Feb. 18, 2010

(30) Foreign Application Priority Data

Mar. 3, 2005 (JP) .................................. 2005-059694
Jun. 30, 2005 (JP) .................................. 2005-192757

(51) Int. Cl.
C07D 223/18 (2006.01)
(52) U.S. Cl. ........................................................ 540/543
(58) Field of Classification Search .................... 540/543
See application file for complete search history.

(56) References Cited

U.S. PATENT DOCUMENTS

| 5,332,846 | A | 7/1994 | Devon et al. |
| 5,502,261 | A | 3/1996 | Kleiner et al. |
| 6,063,920 | A | 5/2000 | Aggarwal et al. |
| 6,340,753 | B1 | 1/2002 | Maruoka et al. |
| 2006/0069134 | A1 | 3/2006 | Maruoka et al. |

FOREIGN PATENT DOCUMENTS

| JP | A-61-254606 | 11/1986 |
| JP | A-62-032107 | 2/1987 |
| JP | 8-40954 | 2/1996 |
| JP | 11-510802 | 9/1999 |
| JP | A-2000-154156 | 6/2000 |
| JP | 2001-48866 | 2/2001 |
| JP | 2002-173492 | 6/2002 |
| JP | 2002-326992 | 11/2002 |
| JP | 2003-81976 | 3/2003 |
| JP | 2003-327566 | 11/2003 |
| JP | 2004-131447 | 4/2004 |
| JP | 2004-238362 | 8/2004 |
| JP | 2004-352708 | 12/2004 |
| JP | 2004-359578 | 12/2004 |
| JP | 2005-15402 | 1/2005 |
| JP | 2005-41791 | 2/2005 |
| JP | 2005-225809 | 8/2005 |
| JP | 2005-225810 | 8/2005 |
| JP | 2005-263664 | 9/2005 |
| WO | 93-20695 | 10/1993 |
| WO | WO 2004/031163 A1 | 4/2004 |
| WO | 2004/076459 | 9/2004 |
| WO | 2005/007622 | 1/2005 |
| WO | 2005-073196 | 8/2005 |
| WO | 2005-077908 | 8/2005 |

OTHER PUBLICATIONS

Patani, Bioisosterism: A Rational APproach in Drug Design, 1996, Chem. Rev., 96, p. 3147-3176.*
Fraser et al., "Substitution αto the Nitrogen in Dibenzylamine via Carbanion Intermediates," Can. J. Chem., vol. 51, pp. 1109-1115, 1973.
Meyers et al., "Chiral Oxazoline Route to Enantiomerically Pure Biphenyls: Magnesio and Copper Mediated Asymmetric Hetero- and Homo-Coupling Reactions," Tetrahedron, vol. 60, pp. 4459-4473, 2004.
Jan. 11, 2011 Notice of Reasons for Rejection issued in Japanese Application No. 2007-506022 with English translation.
Ooi et al., "A New N-Spiro $C_2$-Symmetric Chiral Quaternary Ammonium Bromide Consisting of 4,6-Disubstituted Biphenyl Subunit as an Efficient Chiral Phase-Transfer Catalyst," Synlett, No. 12, pp. 1931-1933, 2003.
Jun. 28, 2011 Notice of Reasons for Rejection issued in Japanese Application No. 2007-506022 with English-language translation.
Ooi, et al. Importance of Chiral Phase-Transfer Catalysts with dual Functions in Obtaining High Enantioselectivity in the Michael Reaction of Malonates and Chalcone Derivatives, Organic Letters, vol. 7, No. 15, pp. 3195-3197, 2005.

(Continued)

*Primary Examiner* — Golam M M Shameem
*Assistant Examiner* — Karen Cheng
(74) *Attorney, Agent, or Firm* — Oliff & Berridge, PLC.

(57) ABSTRACT

Disclosed is an optically active quaternary ammonium salt compound represented by the formula (1) below. Also disclosed are a production intermediate of such an optically active quaternary ammonium salt compound, and a method for producing such an optically active quaternary ammonium salt compound. (1) (In the formula, $R^1$, $R^2$, $R^{21}$, $R^3$ and $R^4$ respectively represent an alkyl group, an aryl group or the like; $R^5$ and $R^6$ respectively represent an alkyl group, an alkoxy group or the like; and $X^-$ represents an anion.)

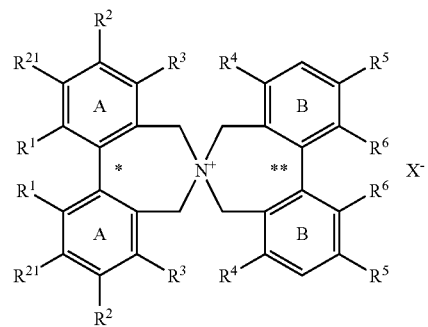

(1)

6 Claims, No Drawings

OTHER PUBLICATIONS

Ooi, et al. Design of New Chiral Phase-Transfer Catalysts with Dual Functions for Highly Enantioselective Epoxidation of a, b-Unsaturated Ketones, J. Am. Chem. Soc., vol. 126, pp. 6844-6845, 2004.

Ooi, et al. Evaluation of the Relationship between the Catalyst Structure and Regio- as well as Stereoselectivity in the chiral Ammonium Biflouride-Catalyzed Asymmetric Addition of Silyl Nitronates to a, b-Unsaturated Aldehydes, Chemistry Letters, vol. 33, No. 7, pp. 824-825.

Ooi, et al. Conformationally Flexible, Chiral Quaternary Ammonium Bromides for Asymmetric Phase-Transfer Catalysis, Angew. Chem. Int. Ed., vol. 41, No. 9, pp. 1551-1554, 2002.

Colletti, et al. Asymmetric Synthesis and Metalation of a Binaphthylcyclopentadiene, a C2-Symmetric Chiral Cyclopentadiene, Organometallics, vol. 10, pp. 3438-3448, 1991.

Ikunaka, et al. A Scalable Synthesis of (R)-3, 5-Dihydro-4H-dinaphth [2,1-c:1'2' -e]azepine, Organic Process Research & Development, vol. 7, pp. 644-648, 2003.

Ooi, et al. Molecular Design of a C2-Symmetric Chiral Phase-Transfer Catalyst for Practical Asymmetric Synthesis of a-Amino Acids, J. Am. Chem. Soc., vol. 121, pp. 6519-6520, 1999.

Ooi et al., "Evaluation of the Relationship between the Catalyst Structure and Regio- as well as Stereoselectivity in the Chiral Ammonium Bifluoride-Catalyzed Asymmetric Addition of Silyl Nitronates to α, β-Unsaturated Aldehydes", Chemistry Letters, vol. 33, No. 7, pp. 824-825, 2004.

* cited by examiner

OPTICALLY ACTIVE AMMONIUM SALT COMPOUND, PRODUCTION INTERMEDIATE THEREOF, AND PRODUCTION METHOD THEREOF

TECHNICAL FIELD

The present invention relates to a compound of an optically active quaternary ammonium salt which is useful as a chiral phase transfer catalyst and more specifically, relates to a novel optically active quaternary ammonium salt, and an intermediate and production method for producing said compound.

Priority is claimed on Japanese Patent Applications No. 2005-059694, filed Mar. 3, 2005, and No. 2005-192757, filed Jun. 30, 2005, the contents of which are incorporated herein by reference.

BACKGROUND ART

Many compounds regarding optically active spiro quaternary ammonium salts have been known to date. Examples thereof include the compound described in Patent document 1 and represented by the following formula

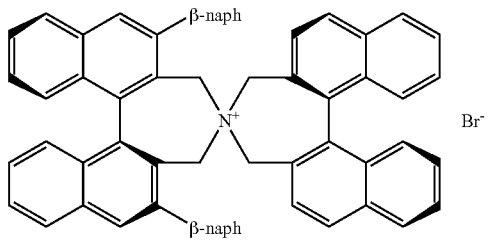

and the compound described in Patent document 3, and the documents disclose that these compounds perform extremely effectively as a phase transfer catalyst for synthesizing optically active α-amino acids regardless of being natural or not. However, the optically active spiro quaternary ammonium salts described in these documents are expensive since they are constituted from two kinds of binaphthyl derivatives having different substituents, and thus they are not necessarily satisfactory for industrial use.

Moreover, the compound represented by the following formula is described in Patent document 2.

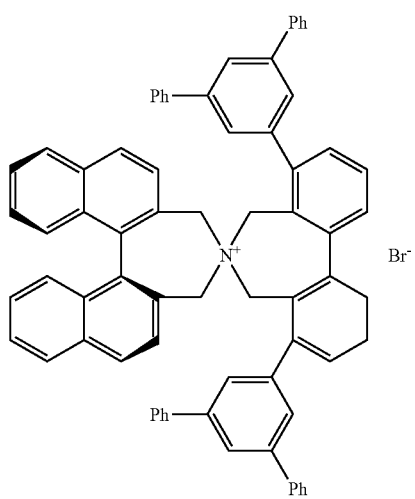

However, because the compound is optically active only on one side, the reaction time is long, and thus the compound is not necessarily satisfactory for industrial use.

Furthermore, the compound represented by the following formula is described in Patent document 4. However, since the spiro quaternary ammonium salts described in these documents are constituted of two kinds of optically active biphenyl derivatives which have the same substituents, there are limits in catalyst design, and thus the salts are not necessarily satisfactory for industrial use.

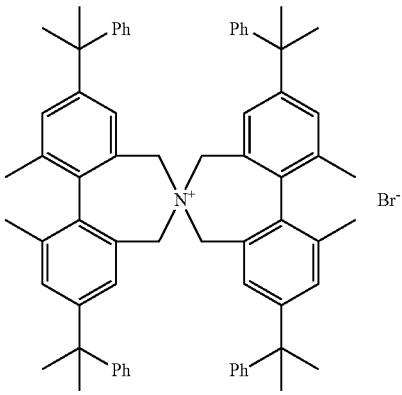

For this reason, the development of an optically active spiro quaternary ammonium salt which is effective as a phase transfer catalyst for synthesizing optically active α-amino acids and which is readily produced and is also practical, has been desired.

[Patent document 1] Japanese Laid-Open Patent Application No. 2001-48866

[Patent document 2] Japanese Laid-Open Patent Application No. 2002-326992

[Patent document 3] Japanese Laid-Open Patent Application No. 2003-81976

[Patent document 4] Japanese Laid-Open Patent Application No. 2004-359578

DISCLOSURE OF THE INVENTION

Problems to be Solved by the Invention

The present invention is made to solve the aforementioned problems of the prior art regarding the compounds of optically active quaternary ammonium salts which are useful as chiral phase transfer catalysts. The object of the present invention is to provide a compound having excellent effects in synthesizing optically active amino acids regardless of being natural or not, and a production method capable of producing said compound to industrial advantage.

Means for Solving the Problem

The present inventors studied intensively in order to solve the above problems and discovered the following to complete the present invention. That is, optically active spiro quaternary ammonium salts, which are constituted from two kinds of biphenyl derivatives having different substituents or from a biphenyl derivative and binaphthyl derivative, and which can be used as a catalyst having excellent effects in synthesizing optically active amino acids and which are industrially useful, as well as a method for readily producing said quaternary ammonium salts.

In the present invention, the discovered method for readily producing the spiro quaternary ammonium salts is based on kinetic resolution. According to said production method, for example, even when a biphenyl derivative, which is a material compound, has no optical activity, a compound of an optically active quaternary ammonium salt having two axial asymmetries can readily be obtained by reacting with an optically active azepine derivative. During this process, it is also possible to recover the biphenyl derivative which is not involved in the reaction as an optically active substance. In addition, when a biphenyl derivative, which is a material compound, has an optical activity, likewise, a compound of an optically active quaternary ammonium salt having two axial asymmetries can readily be obtained by reacting with an azepine derivative which has no optical activity, and it is also possible to recover the azepine derivative, which is not involved in the reaction, as an optically active substance.

Furthermore, another basis constituting the method for readily producing the spiro quaternary ammonium salts which have been discovered in the present invention is the simple production method of azepines which are important production intermediates for producing the spiro quaternary ammonium salts. According to the present production method, by reacting a 2,2'-bis(substituted methyl)biaryl compound, which has a substituent at the 3,3'-positions, with ammonia, corresponding azepines can readily be obtained.

That is, a first aspect of the present invention relates to an optically active quaternary ammonium salt compound represented by the formula (1)

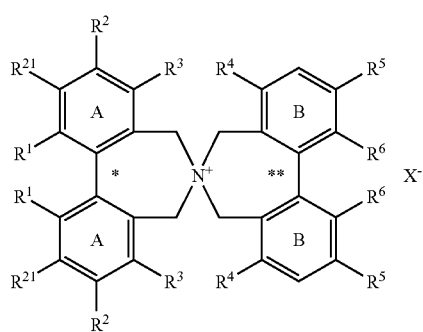

(1)

(in the formula, $R^1$ represents a halogen, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{3-8}$ heteroaryl which is optionally substituted, a $C_{1-8}$ alkoxy which is optionally substituted and which is linear, branched, or cyclic, or a $C_{7-16}$ aralkyl which is optionally substituted;

$R^2$ and $R^{21}$ each independently represents hydrogen, halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, or a $C_{7-16}$ aralkyl which is optionally substituted and one of combinations of $R^1$ and $R^{21}$, and $R^2$ and $R^{21}$, may bind to form a $C_{1-6}$ alkylene which is optionally substituted, a $C_{1-6}$ alkylenemonooxy which is optionally substituted, or a $C_{1-6}$ alkylenedioxy which is optionally substituted;

$R^3$ and $R^4$ each independently represents hydrogen, a $C_{6-14}$ aryl which is optionally substituted, a $C_{3-8}$ heteroaryl which is optionally substituted, or a $C_{7-16}$ aralkyl which is optionally substituted, with a proviso that $R^3$ and $R^4$ are not hydrogen at the same time;

$R^5$ represents hydrogen, halogen, a $C_{1-8}$ alkyl which is optionally substituted and which is linear, branched, or cyclic, a $C_{1-8}$ alkoxy which is optionally substituted and which is linear, branched, or cyclic, a $C_{2-8}$ alkenyl which is optionally substituted, or a $C_{2-8}$ alkynyl which is optionally substituted;

$R^6$ represents halogen, a $C_{1-8}$ a alkyl which is optionally substituted and which is linear, branched, or cyclic, a $C_{1-8}$ alkoxy which is optionally substituted and which is linear, branched, or cyclic, a $C_{2-8}$ alkenyl which is optionally substituted, or a $C_{2-8}$ alkynyl which is optionally substituted, and $R^5$ and $R^6$ may bond to form an aromatic ring which is optionally substituted;

ring A and ring B do not have a same substituent at the same time;

symbols * and ** represent an optical activity having an axial chirality; and $X^{-1}$ represents an anion).

As the quaternary ammonium salt compound represented by the formula (1) the following compounds are preferable:

a compound in which $R^2$ is hydrogen and $R^{21}$ is halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, or a $C_{7-16}$ aralkyl which is optionally substituted;

a compound in which $R^1$, $R^2$, and $R^{21}$ each independently represents a $C_{1-8}$ alkoxy which is optionally substituted and which is linear, branched, or cyclic;

a compound in which $R^1$ is a $C_{1-8}$ alkoxy which is optionally substituted and which is linear, branched, or cyclic, and $R^2$ and $R^{21}$ bond to form a $C_{1-6}$ alkylenedioxy which is optionally substituted;

a compound in which $R^1$ and $R^{21}$ each independently represents a $C_{1-8}$ alkoxy which is optionally substituted and which is linear, branched, or cyclic, and $R^2$ is hydrogen;

a compound in which $R^1$ and $R^{21}$ bond to form a $C_{1-8}$ alkylenedioxy which is optionally substituted, and $R^2$ is hydrogen, fluorine, chlorine, a $C_{1-8}$ alkyl which is optionally substituted and which is linear, branched, or cyclic, a $C_{1-8}$ alkoxy which is optionally substituted and which is linear, branched, or cyclic, or a $C_{7-16}$ aralkyl which is optionally substituted;

a compound in which $R^1$ is fluorine, chlorine, a $C_{1-8}$ alkyl which is optionally substituted and which is linear, branched, or cyclic, or a $C_{1-8}$ alkoxy which is optionally substituted and which is linear, branched, or cyclic, and $R^2$ and $R^{21}$ bond to form a $C_{1-6}$ alkylenedioxy which is optionally substituted;

a compound in which $R^3$ represents a $C_{6-14}$ aryl (which is optionally substituted by halogen, a $C_{1-8}$ alkyl which is optionally substituted by halogen and which is linear, branched, or cyclic, or a $C_{6-14}$ aryl), a $C_{3-8}$ heteroaryl (which is optionally substituted by halogen, a $C_{1-8}$ alkyl which is optionally substituted by halogen and which is linear, branched, or cyclic, or a $C_{6-14}$ aryl), or a $C_{7-16}$ aralkyl (which is optionally substituted by halogen, a $C_{1-8}$ alkyl which is optionally substituted by halogen and which is linear, branched, or cyclic, or a $C_{6-14}$ aryl); and $R^4$ is hydrogen;

a compound in which $R^3$ represents hydrogen and $R^4$ is a $C_{6-14}$ aryl (which is optionally substituted by halogen, a $C_{1-8}$ alkyl which is optionally substituted by halogen and which is linear, branched, or cyclic, or a $C_{6-14}$ aryl), a $C_{3-8}$ heteroaryl (which is optionally substituted by halogen, a $C_{1-8}$ alkyl which is optionally substituted by halogen and which is linear, branched, or cyclic, or a $C_{6-14}$ aryl), or a $C_{7-16}$ aralkyl (which is optionally substituted by halogen, a $C_{1-8}$ alkyl which is optionally substituted by halogen and which is linear, branched, or cyclic, or a $C_{6-14}$ aryl); and a compound in which $X^-$ is an anion of halogen, $OH^-$, $BF_4^-$, $PF_6^-$, $HSO_4^-$, an anion of $C_{1-6}$ dialkylsulfate which is optionally substituted and which is linear, branched, or cyclic, an anion of $C_{1-6}$ alkylsulfonate which is optionally substituted and which is linear, branched, or cyclic, an anion of $C_{6-14}$ arylsulfonate which is optionally substituted, or an anion of $C_{7-16}$ aralkylsulfonate which is optionally substituted.

In addition, a second aspect of the present invention relates to:

(i) an optically active bisbenzyl compound or a racemic bisbenzyl compound represented by the formula (2)

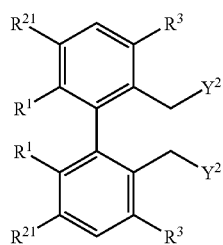

(2)

(in the formula, $R^1$, $R^{21}$, and $R^3$ are the same as above and $Y^2$ represents a leaving group) which has axial chirality; and (ii) a racemic azepine derivative or an optically active azepine derivative represented by the formula (3)

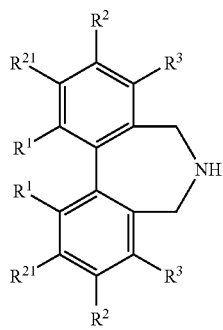

(3)

(in the formula, $R^1 R^2$, $R^{21}$, and $R^3$ are the same as above).

A third aspect of the present invention is a production method of an azepine derivative characterized in that a biphenyl derivative represented by the formula (4)

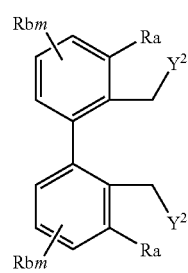

(4)

(in the formula, Ra represents a $C_{6-14}$ aryl which is optionally substituted, a $C_{3-8}$ heteroaryl which is optionally substituted, or a $C_{7-16}$ aralkyl which is optionally substituted; Rb represents halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, or a $C_{7-16}$ aralkyl which is optionally substituted, and Rb may bond with each other to form a $C_{1-6}$ alkylene which is optionally substituted, a $C_{1-6}$ alkylenemonooxy which is optionally substituted, a $C_{1-6}$ alkylenedioxy which is optionally substituted, or an aromatic ring which is optionally substituted; and m is 0 or represents an integer of 1 to 3 and Rb may be different substituents to each other when m is 2 or more); and ammonia are reacted to produce the azepine derivative represented by the following formula (5)

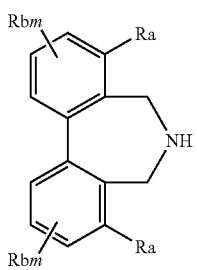

(5)

(in the formula, Ra, Rb, and m are the same as above). This azepine derivative is useful as a production intermediate of the compound represented by the formula (1), A fourth aspect of the present invention is a production method of an optically active quaternary ammonium salt compound characterized in that, (i) an optically active bisbenzyl derivative represented by the formula (6)

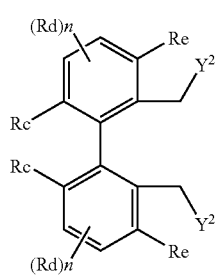

(6)

(in the formula, Rc represents halogen, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{3-8}$ heteroaryl which is optionally substituted, a $C_{1-8}$ alkoxy which is optionally substituted and which is linear, branched, or cyclic, or a $C_{7-16}$ aralkyl which is optionally substituted; Rd and Re each independently represents halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, a $C_{3-8}$ heteroaryl which is optionally substituted, or a $C_{7-16}$ aralkyl which is optionally substituted, and Rd may bond with each other to form a $C_{1-6}$ alkylene which is optionally substituted, a $C_{1-6}$ alkylenemonooxy which is optionally substituted, or a $C_{1-6}$ alkylenedioxy which is optionally substituted, and n is 0 or represents an integer of 1 to 2 and Rd may be different substituents to each other when n is 2; and $Y^2$ is the same as above);

and racemic azepine derivative represented by the formula (7)

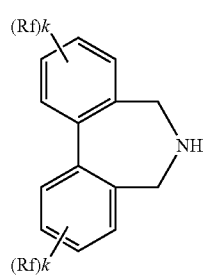

(7)

(in the formula, Rf represents halogen, a $C_{1-8}$ alkyl which is optionally substituted and which is linear, branched, or cyclic, a $C_{1-8}$ alkoxy which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{3-8}$ heteroaryl which is optionally substituted, or a $C_{7-16}$ aralkyl which is optionally substituted, and k is 0 or represents an integer of 1 to 4 and Rf may be different substituents to each other when k is 2 or more and Rf may bond with each other to form an aromatic ring which is optionally substituted); are reacted to produce the optically active quaternary ammonium salt compound represented by the formula (8)

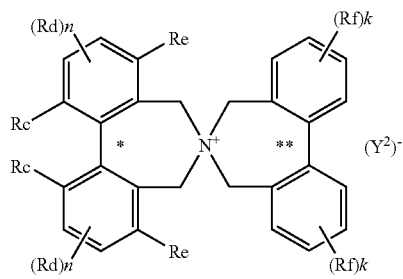

(8)

(in the formula, Rc, Rd, Re, Rf, n, k, and symbols * and ** are the same as above); and (ii) the production method of an optically active quaternary ammonium salt compound represented by the formula (8) characterized in that the racemic bisbenzyl derivative represented by the formula (6) and optically active azepine derivative represented by the formula (7) are reacted.

A fifth aspect of the present invention is a production method of an optically active quaternary ammonium salt compound characterized in that an optically active azepine derivative represented by the formula (9)

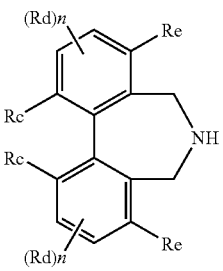

(9)

(in the formula, Rc, Rd, and n are the same as above); and racemic bisbenzyl derivative represented by the following formula (10)

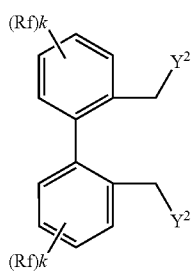

(10)

(Rf, k, and $Y^2$ are the same as above); are reacted to produce the optically active quaternary ammonium salt compound represented by the following formula (8)

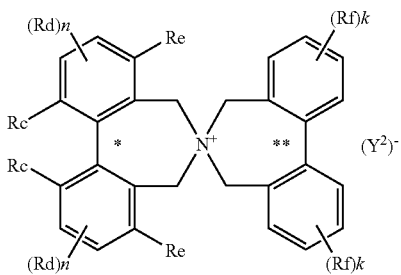

(8)

(in the formula, Rc, Rc, Re, Rf, n, k, and symbols * and ** are the same as above); and (ii) a production method of the optically active quaternary ammonium salt compound represented by the formula (8) characterized in that the racemic bisbenzyl derivative represented by the formula (9) and optically active azepine derivative represented by the formula (10) are reacted.

Effects of the Invention

The optically active quaternary ammonium salt compound of the present invention can be produced in an industrially advantageous method and has an excellent catalytic effect on the synthesis of optically active amino acids.

In addition, according to the production method of the present invention, the compounds of optically active quaternary ammonium salts can be industrially advantageously produced due to kinetic resolution

BEST MODES FOR CARRYING OUT THE INVENTION

The present invention will be described in detail below.

Examples of halogens in the present specification include each atom of fluorine, chlorine, bromine, and iodine.

Examples of the $C_{1-8}$ alkyl, which is linear, branched, or cyclic, of the $C_{1-8}$ alkyl which is linear, branched, or cyclic, and which is optionally substituted, include methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, and cyclohexyl.

Examples of the $C_{2-8}$ alkenyl of the $C_{2-8}$ alkenyl, which is optionally substituted, include vinyl, 1-propenyl, 2-propenyl, isopropenyl, 1-butenyl, 2-butenyl, 3-butenyl, 1-pentenyl, 2-pentenyl, 3-pentenyl, 4-pentenyl, 1-methyl-2-butenyl, 1-methyl-3-butenyl, 1,1-dimethyl-2-propenyl, 3-methyl-2-butenyl, 1-hexenyl, 2-hexenyl, 3-hexenyl, 4-hexenyl, 5-hexenyl, 2-methyl-1-pentenyl, 3-methyl-1-pentenyl, 4-methyl-1-pentenyl, 2-methyl-2-pentenyl, 3-methyl-2-pentenyl, 2-ethyl-1-butenyl, 3,3-dimethyl-1-butenyl, 1-heptenyl, 2-heptenyl, 3-heptenyl, 1-octenyl, 2-octenyl, 3-octenyl, and 4-octenyl.

Examples of the $C_{2-8}$ alkynyl of the $C_{2-8}$ alkynyl, which is optionally substituted, include ethynyl, 1-propynyl, 2-propynyl, 1-butynyl, 2-butynyl, 3-butynyl, 1-pentynyl, 2-pentynyl, 3-pentynyl, 4-pentynyl, 4-methyl-1-pentynyl, 1-hexynyl, and 1-octynyl.

Examples of the $C_{6-14}$ aryl of the $C_{6-14}$ aryl, which is optionally substituted, include phenyl, 1-naphthyl 2-naphthyl, 1-anthryl, 2-anthryl, 9-anthryl, 1-phenanthryl, 2-phenanthryl, 3-phenanthryl, 4-phenanthryl, 9-phenanthryl, and 10-phenanthryl.

The $C_{3-8}$ heteroaryl of the $C_{3-8}$ heteroaryl, which is optionally substituted, is monocyclic, polycyclic, or a condensed ring which contains 1 to 4 atoms of N, O, and S and these atoms may be the same or different. Specific examples of the $C_{3-8}$ heteroaryl include 2-pyridyl, 3-pyridyl, 4-pyridyl, 2-quinonyl, 3-quinonyl, 4-quinonyl, 5-quinonyl, 6-quinonyl, 7-quinonyl, 8-quinonyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, and 5-thiazolyl.

The alkyl moiety of the $C_{1-8}$ alkoxy, which is linear, branched, or cyclic, of the $C_{1-8}$ alkoxy which is linear, branched, or cyclic, and which is optionally substituted, is the same as the aforementioned alkyl. Specific examples of the $C_{1-8}$ alkoxy include methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, cyclopentyloxy, and cyclohexyloxy.

Examples of the $C_{7-16}$ aralkyl of the $C_{7-16}$ aralkyl, which is optionally substituted, include benzyl, 1-phenylethyl, 2-phenylethyl, 1-methyl-1-phenylethyl, 1-naphthylmethyl, and 2-naphthylmethyl.

Examples of $X^-$ include anions such as anions of halogens like fluorine, chlorine, bromine, and iodine; $OH^-$; $BF_4^-$; $PF_6^-$; $SCN^-$; $HSO_4^-$; anions of $C_{1-6}$ dialkyl sulfate which is optionally substituted and which is linear, branched, or cyclic; anions of $C_{1-6}$ alkyl sulfonate which is optionally substituted and which is linear, branched, or cyclic; anions of $C_{6-14}$ aryl sulfonate which is optionally substituted; and anions of $C_{7-16}$ aralkyl sulfonate which is optionally substituted.

The alkyl moieties of $C_{1-6}$ dialkyl sulfate which is optionally substituted and which is linear, branched, or cyclic and of $C_{1-6}$ alkyl sulfonate which is optionally substituted and which is linear, branched, or cyclic are the same as the aforementioned alkyl. Specific examples of the $C_{1-6}$ dialkyl sulfate and $C_{1-6}$ alkyl sulfonate include dimethyl sulfate, methyl sulfonate, ethyl sulfonate, propyl sulfonate, and butyl sulfonate.

The aryl moiety of $C_{6-14}$ aryl sulfonate group which is optionally substituted is the same as the aforementioned aryl. Specific examples of the $C_{6-14}$ aryl sulfonate include phenylsulfonate, p-toluenesulfonate, and naphthylsulfonate.

The aralkyl moiety of $C_{7-16}$ aralkyl sulfonate group which is optionally substituted is the same as the aforementioned aralkyl. Specific examples of the $C_{7-16}$ aralkyl sulfonate include benzylsulfonate and phenethylsulfonate.

Examples of the aromatic ring which is formed by the bonding of $R^5$ and $R^6$ and which is optionally substituted include a benzene ring and naphthalene ring.

The $C_{1-6}$ alkylene of the $C_{1-6}$ alkylene, which is optionally substituted, is represented by the formula $—(CH_2)_n—$ (in the formula, n represents an integer of 1 to 6). Specific examples of the compounds, in which $R^1$ and $R^{21}$ or $R^2$ and $R^{21}$ are bonded, include the compounds having the following structures.

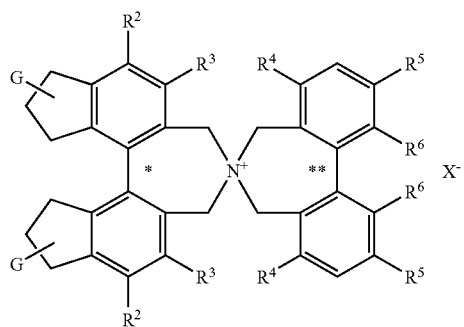
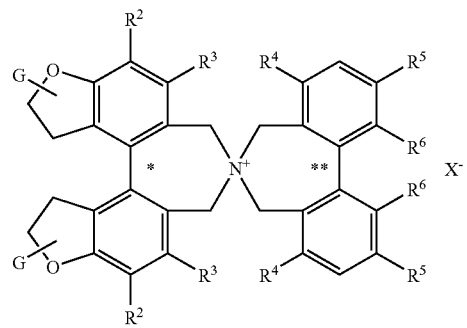
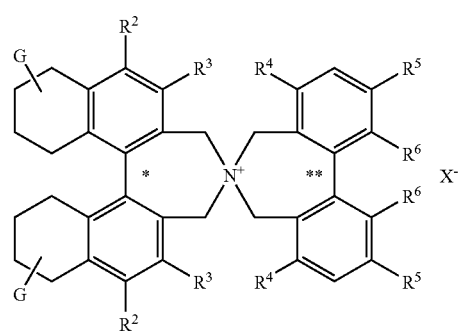
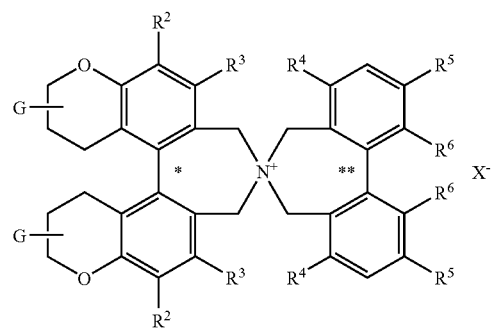
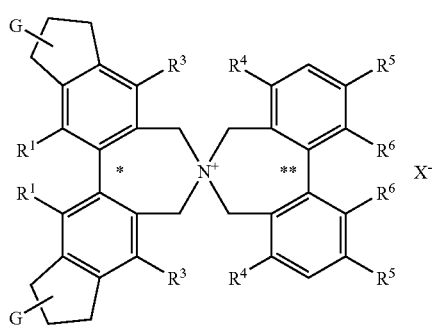
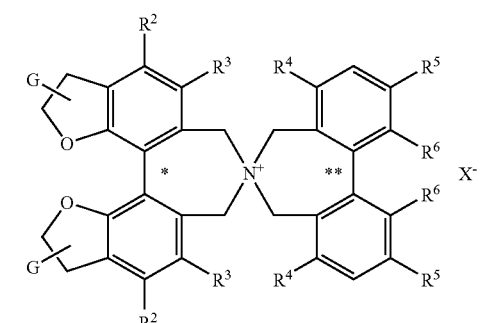
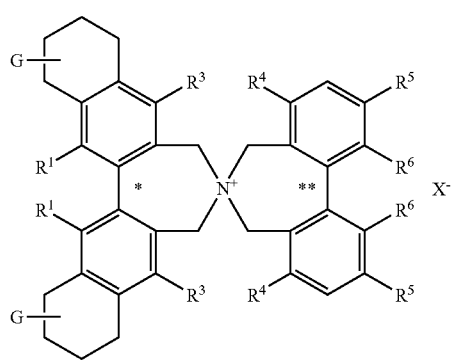
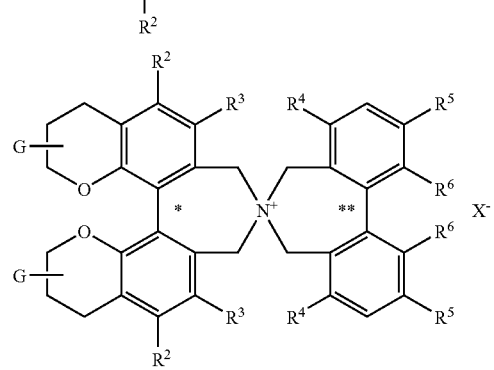
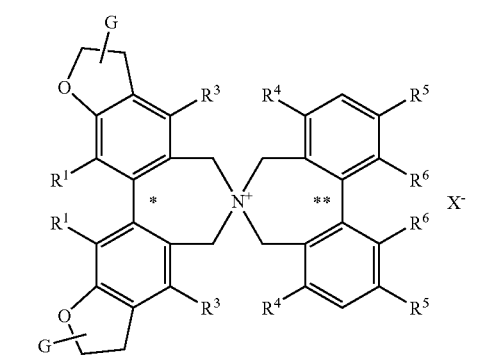

(In the formula, G represents a substituent.)

The $C_{1-6}$ alkylenemonooxy of the $C_{1-6}$ alkylenemonooxy, which is optionally substituted, is represented by the formula —O(CH$_2$)$_n$— or —(CH$_2$)$_n$O— (in the formula, n represents an integer of 1 to 6). Specific examples of the compounds, in which $R^1$ and $R^{21}$ or $R^2$ and $R^{21}$ are bonded, include the compounds having the following structures.

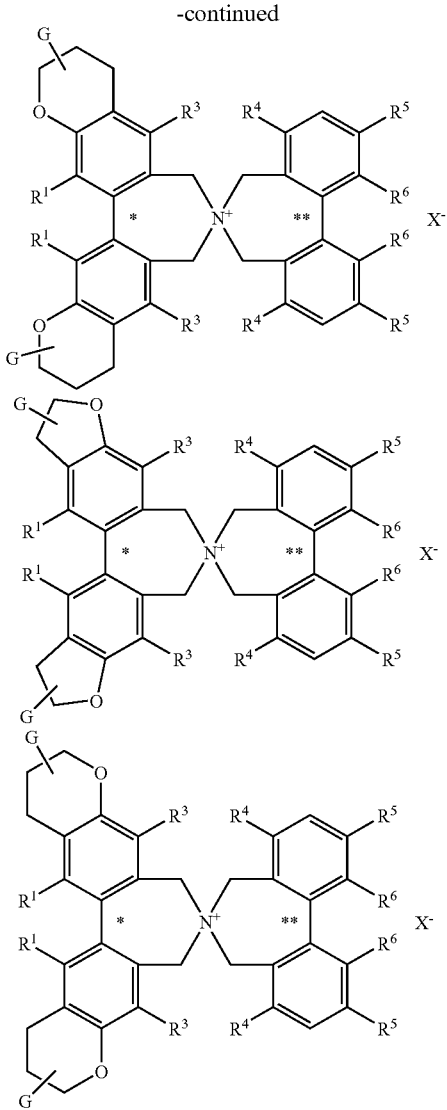

(In the formula, G represents a substituent.)

The $C_{1-6}$ alkylenedioxy of the $C_{1-6}$ alkylenedioxy, which is optionally substituted, is represented by the formula —O(CH$_2$)$_n$O— (in the formula, n represents an integer of 1 to 6). Specific examples of the compounds, in which $R^1$ and $R^{21}$ or $R^2$ and $R^{21}$ are bonded, include the compounds having the following structures.

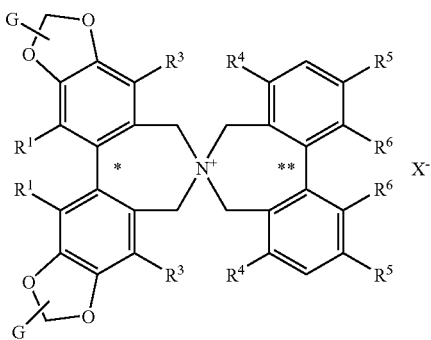

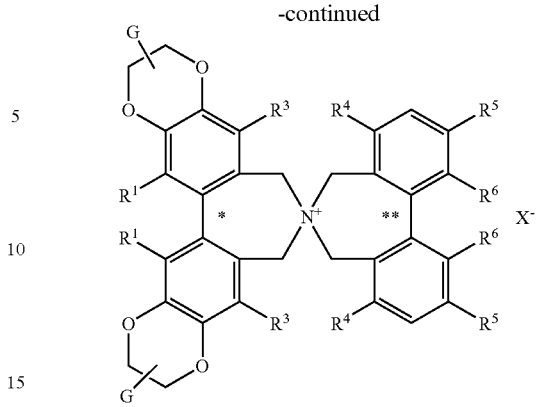

(In the Formula, G represents a substituent.)

Additionally, the leaving group represents halogen, a $C_{1-8}$ alkylsulfonyloxy which is optionally substituted, $C_{6-14}$ arylsulfonyloxy which is optionally substituted, $C_{7-16}$ aralkylsulfonyloxy which is optionally substituted, or the like.

The alkyl moiety, aryl moiety, and aralkyl moiety in the $C_{1-8}$ alkylsulfonyloxy which is optionally substituted and which is linear, branched, or cyclic, $C_{6-14}$ arylsulfonyloxy which is optionally substituted, and $C_{7-16}$ aralkylsulfonyloxy which is optionally substituted, are the same alkyl, aryl, and aralkyl as defined above, respectively.

The group which is optionally substituted (i.e., $C_{1-8}$ alkyl, $C_{2-8}$ alkenyl, $C_{2-8}$ alkynyl, $C_{6-14}$ aryl, $C_{3-8}$-heteroaryl, $C_{1-8}$ alkoxy, $C_{7-16}$ aralkyl, aromatic rings formed by the bonding of $R^5$ and $R^6$, $C_{1-6}$ alkylene, $C_{1-6}$ alkylenemonooxy, $C_{1-6}$ alkylenedioxy, $C_{1-6}$ dialkyl sulfate group, $C_{1-6}$ alkylsulfonate group, $C_{6-14}$ arylsulfonate group, $C_{7-16}$ aralkylsulfonate group, $C_{1-6}$ alkylsulfonyloxy group, $C_{6-14}$ arylsulfonyloxy group, and $C_{7-16}$ aralkylsulfonyloxy group) and substituent G are the substituent which may be substituted at 1 to 6 positions by the same or different substituents, and examples thereof include:

halogens such as fluorine, chlorine, bromine, and iodine;

$C_{1-8}$ alkyl which is linear, branched, or cyclic, such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl;

$C_{1-5}$ perfluoroalkyl which is linear, branched, or cyclic, such as trifluoromethyl, tetrafluoroethyl, and heptafluoroisopropyl;

$C_{6-14}$ aryl such as phenyl, 1-naphthyl, 2-naphthyl, 1-anthryl, 2-anthryl, 9-anthryl, 1-phenanthryl, and 2-phenanthryl;

$C_{1-8}$ alkoxy which is linear, branched, or cyclic, such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy;

$C_{7-16}$ aralkyl such as benzyl, 2-phenylethyl, 1-naphthylmethyl, and 2-naphthylmethyl; and $C_{3-8}$ heteroaryl, which is monocyclic, polycyclic, or a condensed ring which contains 1 to 4 atoms of N, O, and S and these atoms may be the sane or different, such as 2-pyridyl, 3-pyridyl, 4-pyridyl, 2-quinonyl, 3-quinonyl, 4-quinonyl, 5-quinonyl, 6-quinonyl, 7-quinonyl, 8-quinonyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, and 5-thiazolyl.

Examples of the racemic bisbenzyl compound having an axial chirality and represented by the aforementioned formula (2), which is useful as a production intermediate of the compound represented by the aforementioned formula (1), include the compound represented by the following formula (2a), and examples of the optically active bisbenzyl compound include the compound represented by the following formula (2b).

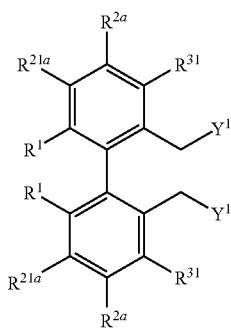

(2a)

In the formula,
R$^1$ is the same as above;
R$^{2a}$ and R$^{21a}$ each independently represents halogen, a C$_{1-8}$ alkyl which is optionally substituted and which is linear, branched, or cyclic, a C$_{2-8}$ alkenyl which is optionally substituted, a C$_{2-8}$ alkynyl which is optionally substituted, a C$_{6-14}$ aryl which is optionally substituted, a C$_{3-8}$ heteroaryl which is optionally substituted, a C$_{1-8}$ alkoxy which is optionally substituted and which is linear, branched, or cyclic, or a C$_{7-16}$ aralkyl which is optionally substituted;
R$^{31}$ represents a C$_{6-14}$ aryl which is optionally substituted, a C$_{3-8}$ heteroaryl which is optionally substituted, or a C$_{7-16}$ aralkyl which is optionally substituted; and
Y$^1$ represents a leaving group and preferably represents halogen, a C$_{1-8}$ alkylsulfonyloxy which is optionally substituted, a C$_{6-14}$ arylsulfonyloxy which is optionally substituted, or a C$_{7-16}$ aralkylsulfonyloxy which is optionally substituted.

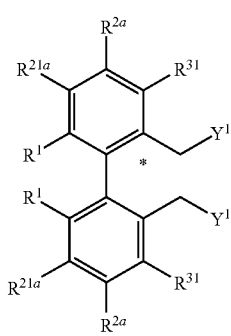

(2b)

In the formula, R$^1$, R$^{2a}$, R$^{21a}$, R$^{31}$, Y$^1$, and the symbol * are the same as above.

Examples of the racemic azepine derivative represented by the aforementioned formula (3), which is useful as a production intermediate of the compound represented by the aforementioned formula (1), include the compound represented by the following formula (3a), and examples of the optically active azepine derivative include the compound represented by the following formula (3b).

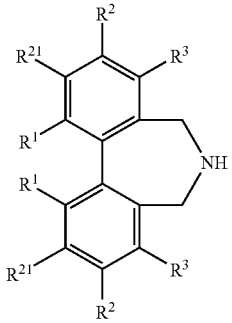

(3a)

In the formula, R$^1$, R$^2$, R$^{21}$, and R$^3$ are the same as above.

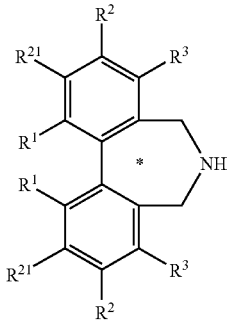

(3b)

In the formula, R$^1$, R$^2$, R$^{21}$, R$^3$, and the symbol * are the same as above.

Since the optically active quaternary ammonium salt compound represented by the aforementioned formula (1) and the following formula (1') (one of the axially asymmetric compounds, which are enantiomorphic, is in excess compared to the other) are constituted by an optically active and axially asymmetric biphenyl and optically active and axially asymmetric binaphthyl, or by 2 kinds of optically active and axially asymmetric biphenyl groups, 4 kinds of isomers of said compound exist; i.e., S,S-form, R,R-form, S,R-form, and R,S-form following the conventional symbols showing an axially asymmetric optical activity, and all these isomers are included in the present invention.

The quaternary ammonium salt compound (1') of the present invention can be produced, for example, by any one the following methods.

(i) Reacting a racemic bisbenzyl compound (2a') and optically active azepine derivative (5b)

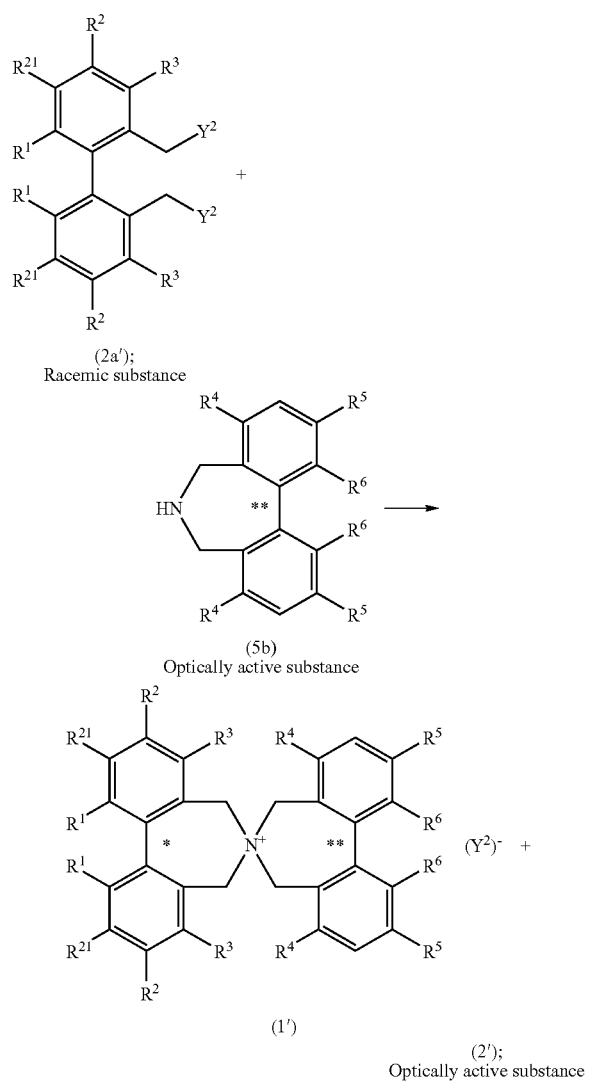

(2a');
Racemic substance (5b)
Optically active substance (1')

(2');
Optically active substance (ii) Reacting an optically active bisbenzyl compound (2b') and racemic azepine derivative (5a)

(2b'); optically active substance+(5a); racemic substance→ (1')+(5b); optically active substance (iii) Reacting a racemic azepine derivative (3a) and optically active biphenyl derivative (4b)

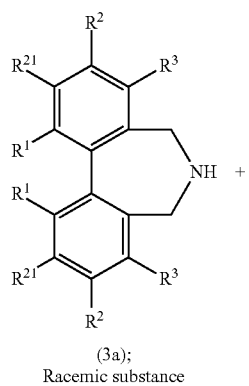

(3a);
Racemic substance

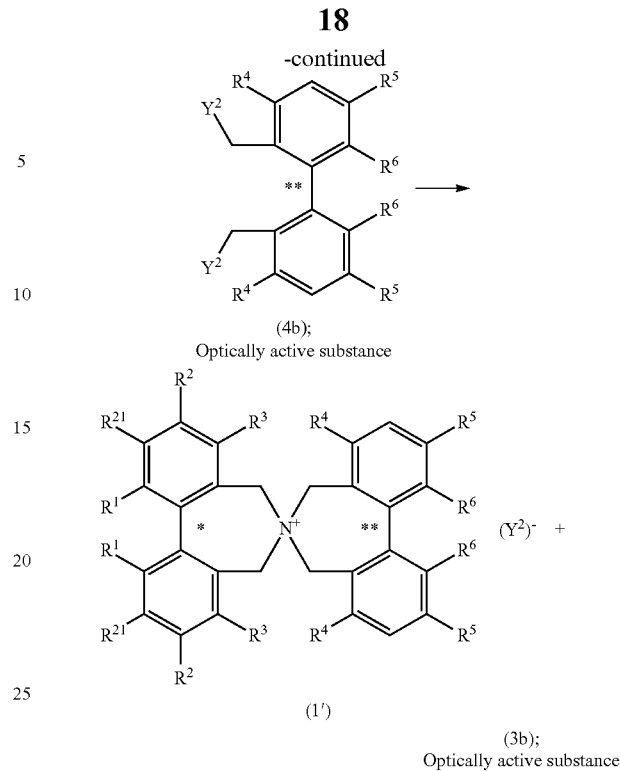

(4b);
Optically active substance (1')

(3b);
Optically active substance (iv) Reacting an optically active azepine derivative (3b) and racemic biphenyl derivative (4a)

(3b); optically active substance+(4a); racemic substance→ (1')+(4b); optically active substance In all the production methods (i) to (iv) of the present invention, when optically active materials are reacted with each other, two asymmetric axes of the obtained quaternary ammonium salt compound are both optically active. However, even when one material, which is optically active, is reacted with another material, which is racemic, the former preferentially reacts with one enantiomer of the latter due to kinetic resolution and two asymmetric axes of the obtained quaternary ammonium salt compound are produced so that they are both optically active. For this reason, the enantiomer of the latter material which is not involved in the production is recovered as an optically active substance. Accordingly, in the production method of the present invention, even when one material is not optically active, the quaternary ammonium salt compound having two asymmetric axes which are both optically active can readily be obtained, and thus it is an advantageous method industrially.

1 to 10 times of the racemic substance in the present invention can be used relative to the optically active substance in terms of moles, and particularly, the use of 1.5 to 3 times in terms of moles is preferable industrially.

The present reaction can be carried out under the presence of a solvent or without a solvent. Usable solvents are not particularly limited as long as they are solvents inert to the reaction and examples thereof include hydrocarbon solvents such as pentane, hexane, heptane, benzene, toluene, and xylene; halogen solvents such as dichloromethane, 1,2-dichloroethane, chloroform, and carbon tetrachloride; alcohols such as methanol and ethanol; nitrile solvents such as acetonitrile and propionenitrile; ether solvents such as diethylether, dioxane, and tetrahydrofuran; non-protonic polar solvents such as N,N-dimethylformamide and dimethylsulfoxide; water; and mixed solvent systems in which two or more of these solvents are mixed.

Examples of the bases include inorganic bases such as sodium hydroxide, potassium hydroxide, sodium carbonate, potassium carbonate, sodium bicarbonate, and potassium bicarbonate; and organic bases such as pyridine, triethylamine, N,N-dimethylaniline, 4-dimethylaminopyridine, N-methylpyrrolidine, N-methylmorpholine, and 1,8-diazabicyclo(5.4.0)undeca-7-ene. The amount of base used is normally 1 to 10 times and preferably 1 to 3 times of that of an optically active binaphthyl derivative or optically active biphenyl derivative in terms of moles.

The temperature range of the present reaction is −78° C. to 200° C. and preferably −20° C. to 100° C. The range of reaction time is 30 minutes to 100 hours, although this depends on the amount of reaction agents, temperature, or the like.

Bisbenzyl compounds (2a') and (2b') and biphenyl derivatives (4a) and (4b), which are production intermediates, can be produced from the corresponding materials by following the method described in Japanese Laid-Open Patent Application No. 2003-327566, Japanese Laid-Open Patent Application No. 2004-359578, or the like.

On the other hand, azepine derivatives (3a), (3b), (5a), and (5b), which are production intermediates, can be produced by following the description below.

That is, 3,3'-dihalogeno-2,2'-dianilines (13), which are obtained by halogenating the bisanilines (12) produced from a known substance based on Japanese Laid-Open Patent Application No. 2004-359578, is reacted under the condition of Suzuki coupling described in Japanese Laid-Open Patent Application No. 2001-48866 or the like (refer to J. Organomet. Chem., 1999, 576, 147) to obtain 3,3-disubstituted-2,2'-dianilines (14).

dosuccinimide (NIS), bromine, chlorine, and iodine. Usable solvents are not particularly limited as long as they are solvents inert to the reaction and examples thereof include hydrocarbon solvents such as pentane, hexane, heptane, benzene, toluene, and xylene; halogen solvents such as dichloromethane, 1,2-dichloroethane, chloroform, and carbon tetrachloride; alcohols such as methanol and ethanol; and mixed solvent systems in which two or more of these solvents are mixed, The reaction can be carried out at an appropriate temperature from room temperature to the boiling point of the solvent.

Subsequently, a 3,3'-disubstituted-2,2'-dihalogenated substance (15) is prepared by converting the amino group in 3,3-disubstituted-2,2'-dianilines (14) to halogen using a nitrite, and by treating this substance (15) with a carbon monoxide-Pd catalyst, a 3,3'-disubstituted-2,2'-diester substance (16) is obtained.

The conversion of amino to halogen due to a nitrite can be carried out based on the method described in Japanese Laid-Open Patent Application No. 2004-359578, and the conversion of the 3,3'-disubstituted-2,2'-dihalogenated substance (15) to the 3,3'-disubstituted-2,2'-diester substance (16) can be carried out based on the method described in Synlett (1998) 2, 183.

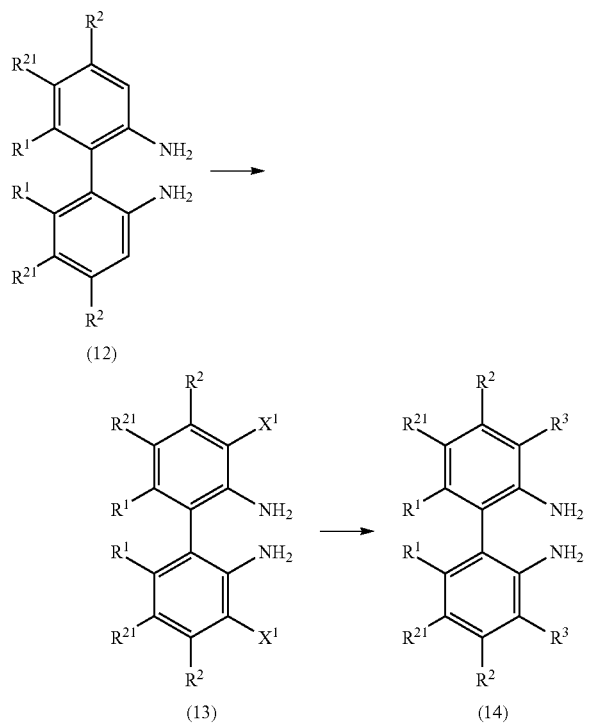

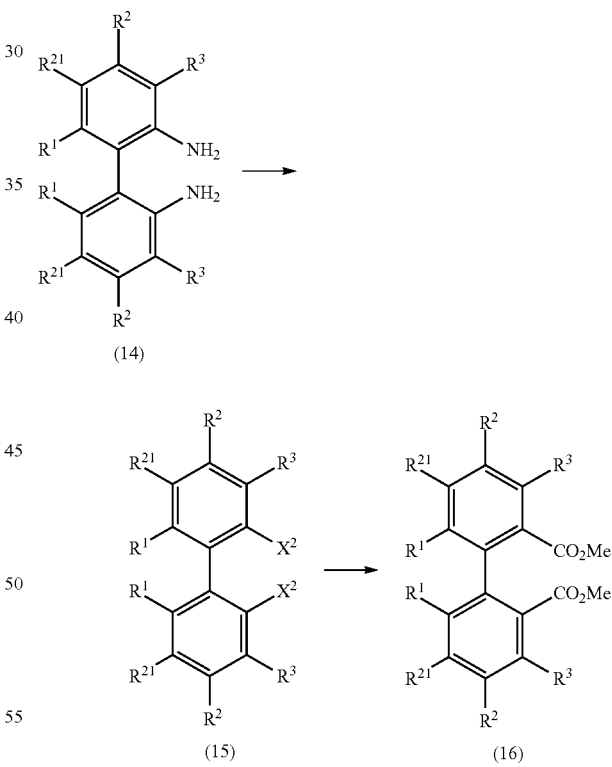

(In the formula, $X^2$ represents halogen and $R^1$, $R^2$, $R^{21}$, and $R^3$ are the same as above.)

Moreover, by carrying out halogenation/Suzuki coupling reaction due to the method according to the above using a known compound or a biphenyl-2,2'-diester substance (14'), which can be derived by known methods, 3,3'-disubstituted-2,2'-diester substance (16) can also be obtained via 3,3'-dihalogenobiphenyl-2,2'-diester substance (15').

(In the Formula, $X^1$ represents halogen and $R^1$, $R^2$, $R^{21}$, and $R^3$ are the same as above.)

Examples of the halogenating reagents include N-bromosuccinimide (NBS), N-chlorosuccinimide (NCS), N-io-

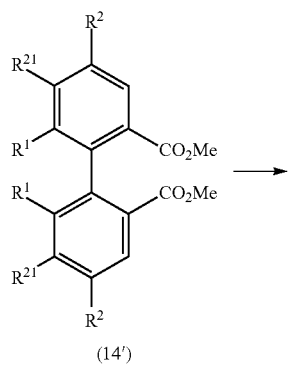

(14')

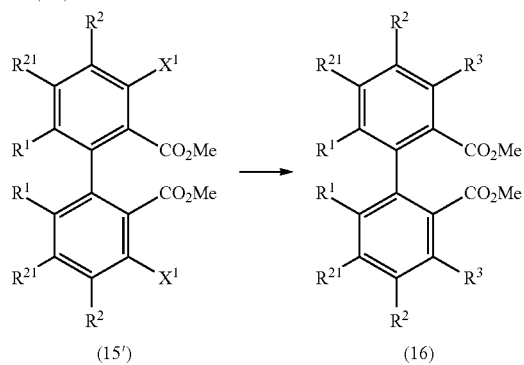

(15') (16)

(In the formula, $X^1$, $R^1$, $R^2$, $R^{21}$, and $R^3$ are the same as above.)

3,3'-disubstituted-2,2'-bishydroxymethyl substance (17) can be obtained by reducing 3,3'-disubstituted-2,2'-diester substance (16) due to the method described in Jikken Kagaku Koza (Courses in Experimental Chemistry, $4^h$ Ed., edited by The Chemical Society of Japan and published by Maruzen Co., Ltd., vol. 20, pp. 10-141).

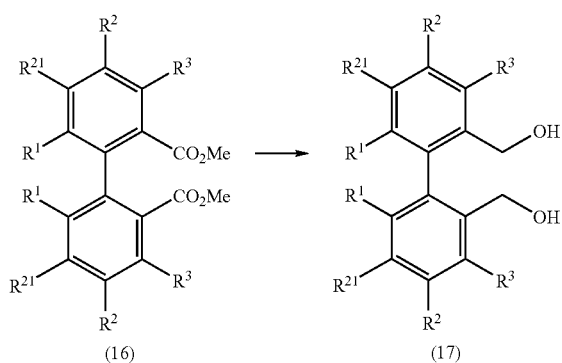

(16) (17)

(In the Formula, $R^1$, $R^2$, $R^{21}$, and $R^3$ are the Same as Above.)

Subsequently, the hydroxyl in 3,3'-disubstituted-2,2'-bishydroxymethyl substance (17) is converted to a leaving group such as halogen based on the method described in Jikken Kagaku Koza (Courses in Experimental Chemistry, $4^{th}$ Ed., edited by The Chemical Society of Japan and published by Maruzen Co., Ltd., vol. 19, pp. 438-445) to obtain a bisbenzyl compound (2a').

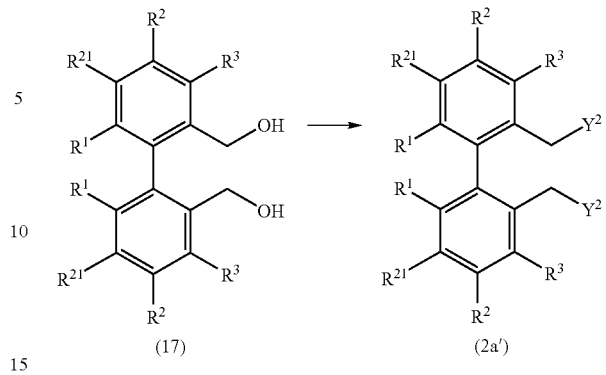

(17) (2a')

(In the formula, $Y^2$ represents a leaving group and $R^1$, $R^2$, $R^{21}$, and $R^3$ are the same as above.)

Examples of the abovementioned leaving group $Y^2$ include halogen, p-toluenesulfonyloxy, and methanesulfonyloxy.

On the other hand, 3,3'-disubstituted-2,2'-dihalogen substance (15) can be converted to 3,3'-disubstituted-2,2'-dimethyl substance (17') according to the method described in a document (J. Mol. Catal., 1990, 60, 343), and the bisbenzyl compound (2a') can also be obtained by subjecting the substance (17') to a general halogenation condition.

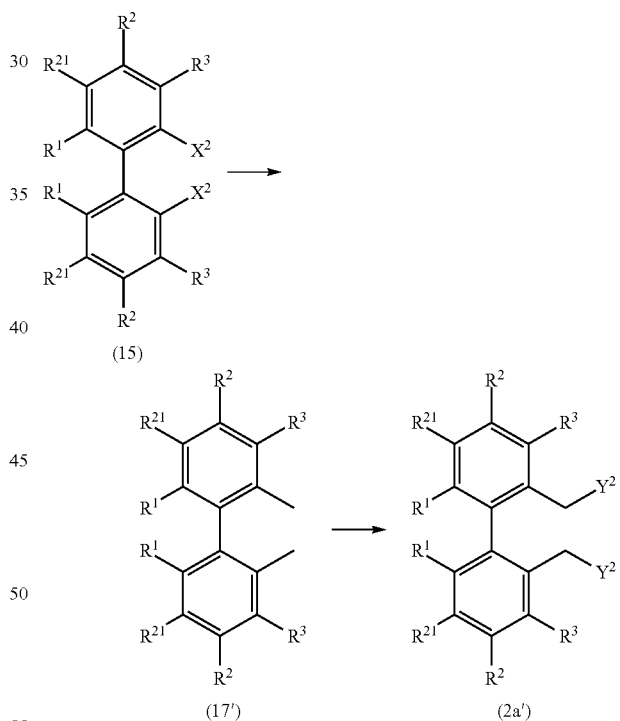

(15)

(17') (2a')

(In the Formula, $R^1$, $R^2$, $R^{21}$, $R^3$, and $Y^2$ are the Same as Above.)

Furthermore, 6,6'-dialkoxy-3,3'-disubstituted-2,2'-dimethyl substance (17") is obtained, for example, by carrying out halogenation/Suzuki coupling reaction according to the aforementioned method using 6,6'-dialkoxy-2,2'-dimethylbiphenyl derivative (14"), which can be synthesized based on a document (J. Chem. Sec., 1950, 711) or the like. By the same treatment carried out on the substance (17') to prepare the substance (2a'), the substance (17") can be derived to a corresponding bisbenzyl compound (2a").

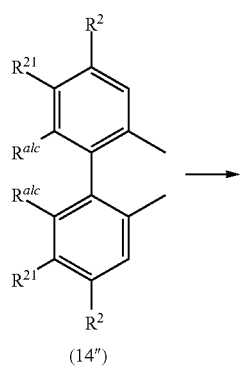

(14″)

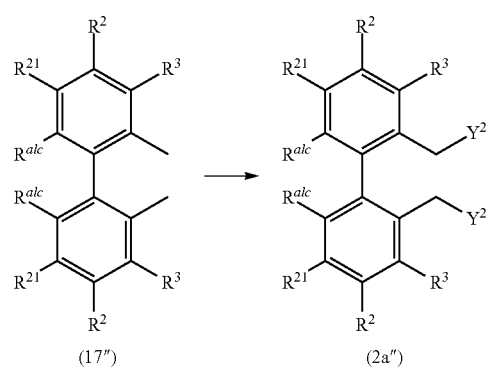

(17″)  (2a″)

(In the formula, $R^{alc}$ represents alkoxy and $R^2$, $R^3$, $R^{21}$, and $Y^2$ are the same as above.)

In addition, it is possible to obtain biphenyl derivatives (4a) from diols (18) according to a document (J. Am. Chem. Soc., 121, 6519 (1999)).

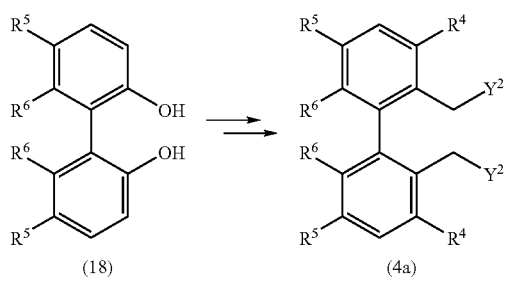

(18)  (4a)

(In the formula, $R^4$, $R^5$, $R^6$, and $Y^2$ are the same as above.)

The synthesis method of the aforementioned bisbenzyl compound (2a') and biphenyl derivatives (4a) can be applied to the corresponding optically-active compounds (2b') and (4b).

By reacting these biphenyls with ammonia, an azepine derivative (3a), (3b), (5a), or (5b) can be produced.

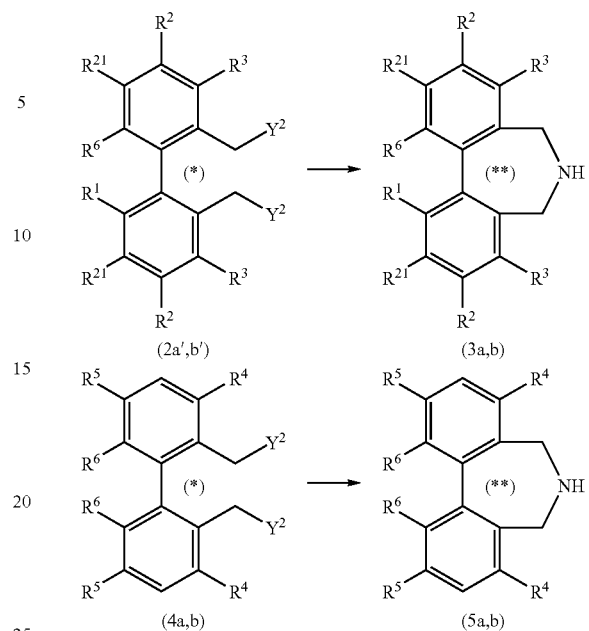

(2a',b')  (3a,b)

(4a,b)  (5a,b)

(In the formula, $R^1$, $R^2$, $R^{21}$, $R^3$, $R^4$, $R^5$, $R^6$, X, and $X^3$ are the same as above and the symbols (*) and (**) represents optical activity when the compound is labeled with the alphabet "b".)

The present reaction can be carried out by reacting the respective solvent solutions of biphenyls and ammonia, or by reacting one with the other's solvent solution directly.

Although the solvent used is not particularly limited as long as it does not react with biphenyls and ammonia, examples thereof include hydrocarbon solvents such as pentane, hexane, heptane, benzene, toluene, and xylene; halogen solvents such as dichloromethane, 1,2-dichloroethane, chloroform, and carbon tetrachloride; alcohols such as methanol and ethanol; nitrile solvents such as acetonitrile and propionenitrile; ether solvents such as diethylether, dioxane, and tetrahydrofuran; non-protonic polar solvents such as N,N-dimethylformamide and dimethylsulfoxide; water; and mixed solvent systems in which two or more of these solvents are mixed. In addition, the solvent for dissolving ammonia is not particularly limited as long as it does not react with ammonia. Examples thereof include hydrocarbon solvents such as pentane, hexane, heptane, benzene, toluene, and xylene; halogen solvents such as dichloromethane, 1,2-dichloroethane, chloroform, and carbon tetrachloride; alcohols such as methanol and ethanol; nitrile solvents such as acetonitrile and propionenitrile; ether solvents such as diethylether, dioxane, and tetrahydrofuran; non-protonic polar solvents such as N,N-dimethylformamide and dimethylsulfoxide; water; and mixed solvent systems in which two or more of these solvents are mixed.

Although the method is not particularly limited, the reaction can be carried out, for example, by adding ammonia, in either gaseous form or liquid form, to the solution of biphenyls directly, or by adding the aforementioned solvent solution of ammonia dropwise to the solution of biphenyls.

Although the mixing ratio of a solvent and biphenyls is not particularly limited, it can appropriately be set from 1:1 to 100:1 (volume:weight). Likewise, ammonia can also be used in an arbitrary concentration.

The mole ratio of biphenyls and ammonia is from 1:0.2 to 1:10 and preferably from 1:1 to 1:5.

Reaction temperature is −70° C. to the boiling point of solvents and preferably −20° C. to 40° C.

After completing the reaction and the distillation process to remove unreacted ammonia, azepine derivatives can be separated/purified by applying known conventional methods such as extraction, washing, distillation, column chromatography, drying, and recrystallization.

The production of an optically active quaternary ammonium salt compound (1) can be carried out by following the condition of a general N-benzylation reaction as shown below.

(a) Reacting an optically active bisbenzyl compound (2b') with an optically active azepine derivative (5b); or (b) Reacting an optically active biphenyl compound (4b) with an optically active azepine derivative (3b)

Additionally, the production of an optically active quaternary ammonium salt compound (1) can also be carried out by the kinetic resolution method. In other words, it can be performed by reacting a racemic substance with an optically active substance as shown below.

(i) Reacting a racemic bisbenzyl compound (2a') with an optically active azepine derivative (5b);

(ii) Reacting an optically active bisbenzyl compound (2b') with a racemic azepine derivative (5a);

(iii) Reacting a racemic azepine derivative (3a) with an optically active biphenyl derivative (4b); or (iv) Reacting an optically active azepine derivative (3b) with a racemic biphenyl derivative (4a)

The reaction between 2 kinds of the aforementioned substances can readily be carried out in an appropriate solvent under the presence of a base.

Solvents can be used regardless of their type as long as they are not involved in the reaction. Examples thereof include hydrocarbon solvents such as pentane, hexan, heptane, benzene, toluene, and xylene; halogen solvents such as dichloromethane, 1,2-dichloroethane, chloroform, and carbon tetrachloride; alcohols such as methanol and ethanol; nitrile solvents such as acetonitrile and propionenitrile; ether solvents such as diethylether, dioxane, and tetrahydrofuran; nonprotonic polar solvents such as N,N-dimethylformamide and dimethylsulfoxide; and mixed solvent systems in which two or more of these solvents are mixed. However, since the present reaction can be carried out under the phase-transfer reaction conditions, solvent systems, in which a water-insoluble solvent among the aforementioned solvents and water are combined, can also be used.

Although general inorganic bases can be used as the base, which may be used, more preferable examples thereof include sodium hydroxide, potassium hydroxide, sodium carbonate, and potassium carbonate.

Reaction can be performed in a solvent or in a solvent system while stirring under the presence of a base, and in a temperature range from the solidifying point to the boiling point of the solvent or the solvent system. Reaction temperature is preferably −20° C. to 80° C. Although reaction time can be adjusted appropriately depending on the reaction temperature, reactions can be completed in 30 minutes to 12 hours.

The volume of the abovementioned reaction solvent is 1 to 100 times larger and more preferably 5 to 50 times larger in terms of volume (ml)/weight (g) ratio with respect to the total weight of the 2 substances.

Although the charged mole ratio of the aforementioned 2 substances is preferably 1:1 when the condition is for a general N-benzylation reaction, more favorable results can be obtained by increasing the amount of one substance, which is more readily available than the other. When using the kinetic resolution method, the ratio of an optically active substance and racemic substance is preferably 1:2 to 1:5 and more preferably 1:2 to 1:3.

The amount of base used is preferably 1 to 6 equivalent and more preferably 1 to 3 equivalent of the leaving group $Y^2$, which is present in the reaction system, when the condition is for a general N-benzylation reaction. When using the kinetic resolution method, the amount of base used is preferably 1 to 6 equivalent and more preferably 1 to 3 equivalent of the leaving group $Y^2$, which is present in the reaction system, if an azepine derivative is an optically active substance, and the amount of base used is preferably 0 to 4 equivalent and more preferably 0 to 1 equivalent of the leaving group $Y^2$, which is present in the reaction system, if the azepine derivative is a racemic substance.

The compound (1) which is produced as such can provide a reaction product having a high optical purity when used as a phase transfer catalyst in the asymmetric alkylation of an α-amino acid derivative.

Although the present invention will be described in more detail below using Examples and Reference Examples, the technical scope of the present invention is not limited to these Examples.

Example 1

Production of 2',2''-bis(bromomethyl)-3,4,5,3''',4''',5'''-hexafluoro-4',5',4'',5''-tetramethyl-(1,1';3',3'';1'',1''')quaterphenyl (22)

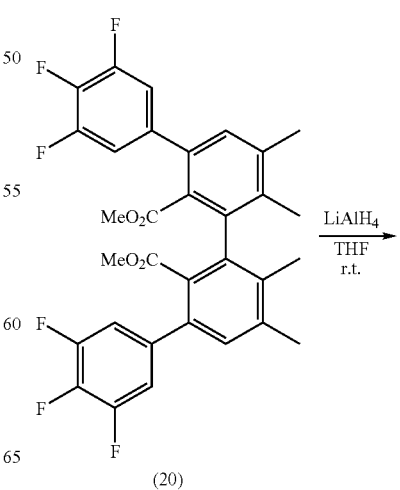

(20)

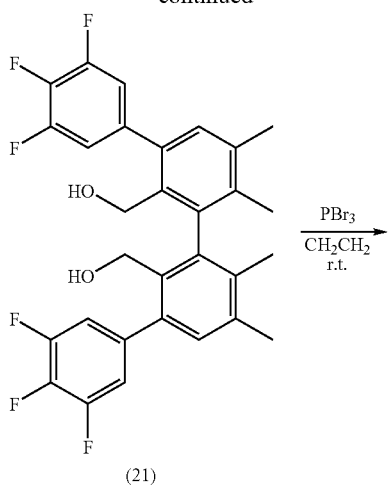

(21)

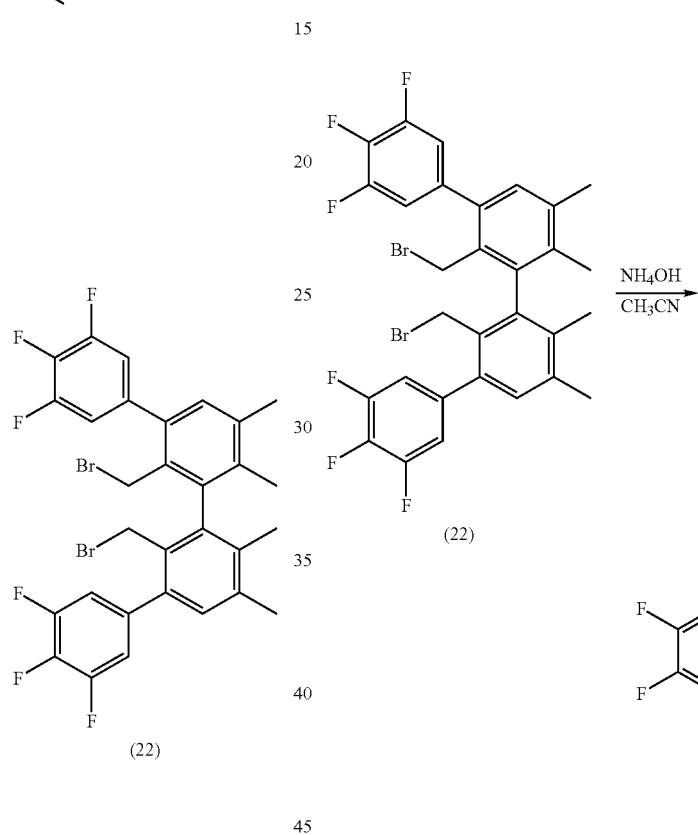

After dissolving 156 mg (0.27 mmol) of a compound (20) in 5 ml of THF and cooling the resultant down to 0° C., 31 mg (0.81 mmol) of LiAlH₄ was added thereto. After increasing the temperature of the mixture slowly to room temperature, the mixture was further stirred for 5 hours. Thereafter, the reaction was stopped by pouring the reaction solution into ice-cold water, and an alcoholic substance (21) was obtained by carrying out further procedures of extraction/drying/concentration. Without subjecting to further purification procedures, the alcoholic substance (21) was dissolved in 5 ml of CH₂Cl₂, and 0.26 ml (0.6 mmol) of PBr₃ was added dropwise to the resulting solution at 0° C. After stirring for 2 hours at room temperature, the reaction solution was poured into ice-cold water to stop the reaction. The reaction solution was then further extracted using methylene chloride and the resultant was dried/concentrated and thereafter purified by column chromatography (ethyl acetate:hexane=1:10) to obtain 137 mg (0.21 mmol) of a compound (22) (yield was 77%).

¹H NMR (300 MHz, CDCl₃), δ7.15 (2H, d, J=6.6 Hz, ArH), 7.12 (2H, d, J=6.6 Hz, ArH), 7.09 (2H, s, ArH), 4.03 (4H, d, J=2.4 Hz, ArCH₂), 2.37 (6H, s, ArCH₃), 1.97 (6H, s, ArCH₃)

Example 2

Production of 1,2,10,11-tetramethyl-4,8-bis(3,4,5-trifluorophenyl)-6,7-dihydro-5H-dibenzo(c,e)azepine

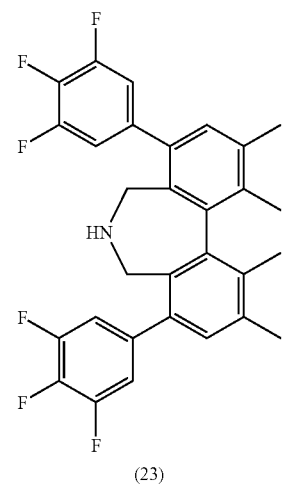

65 mg (0.1 mmol) of the compound (22) and 0.2 ml of 25% ammonia water were stirred in an acetonitrile solvent at room temperature for 24 hours. After the completion of the reaction, the resultant was extracted/dried/concentrated, and thereafter purified by column chromatography (methanol: methylene chloride=1:10) to obtain 51 mg (0.1 mmol) of a compound (23) (yield was 100%).

¹H NMR (300 MHz, CD₃OD), δ7.31 (2H, s, ArH), 7.24 (2H, d, J=6.6 Hz, ArH), 7.21 (2H, d, J=6.6 Hz, ArH), 4.14

(2H, d, J=13.8 Hz, ArCH$_2$), 3.46 (2H, J=3.8 Hz, ArCH$_2$), 2.43 (6H, s, ArCH$_3$), 2.09 (6H, s, ArCH$_3$)

Example 3

Production of optically active quaternary ammonium salt compound (26) (homo)

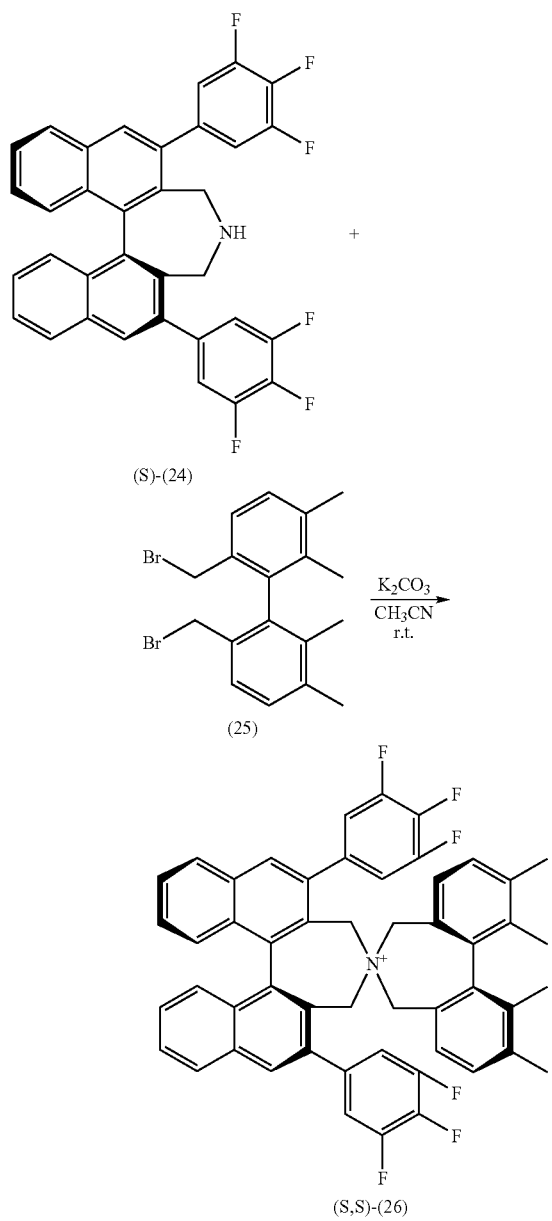

Under the presence of 140 mg of potassium carbonate, 56 mg of a chiral secondary amine (24) and 80 mg of racemic dibromomethylbiphenyl (25), which was 2.1 equivalent of said amine, were stirred in an acetonitrile solvent at room temperature for 12 hours. After the completion of the reaction, the resultant was purified by extraction/column chromatography (methylene chloride:methanol=10:1) to obtain 74 mg of an optically pure compound (S,S)-(26) (yield was 85%).

$[\alpha]_D^{22}$=+25.6° (c1.0, CHCl$_3$)
$^1$H NMR (300 MHz, CDCl$_3$), δ8.21 (2H, s, ArH), 8.08 (21, d, J=8.4 Hz, ArH), 7.205-7.60 (8H, m, ArH), 7.09 (2H, d, J=8.7 Hz, ArH), 6.71 (2H, d, J=7.8 Hz, ArH), 6.02 (2H, d, J=7.8 Hz, ArH), 4.71 (2H, d, J=13.8 Hz, ArCH$_2$), 4.50 (2H, d, J=14.1 Hz, ArCH$_2$), 4.04 (2H, d, J=13.5 Hz, ArCH$_2$), 3.49 (2H, d, J=13.2 Hz, ArCH$_2$), 2.30 (6H, s, ArCH$_3$), 1.88 (6H, s, ArCH$_3$)

Example 4

Production of Optically Active Quaternary Ammonium Salt Compound (29) (homo)

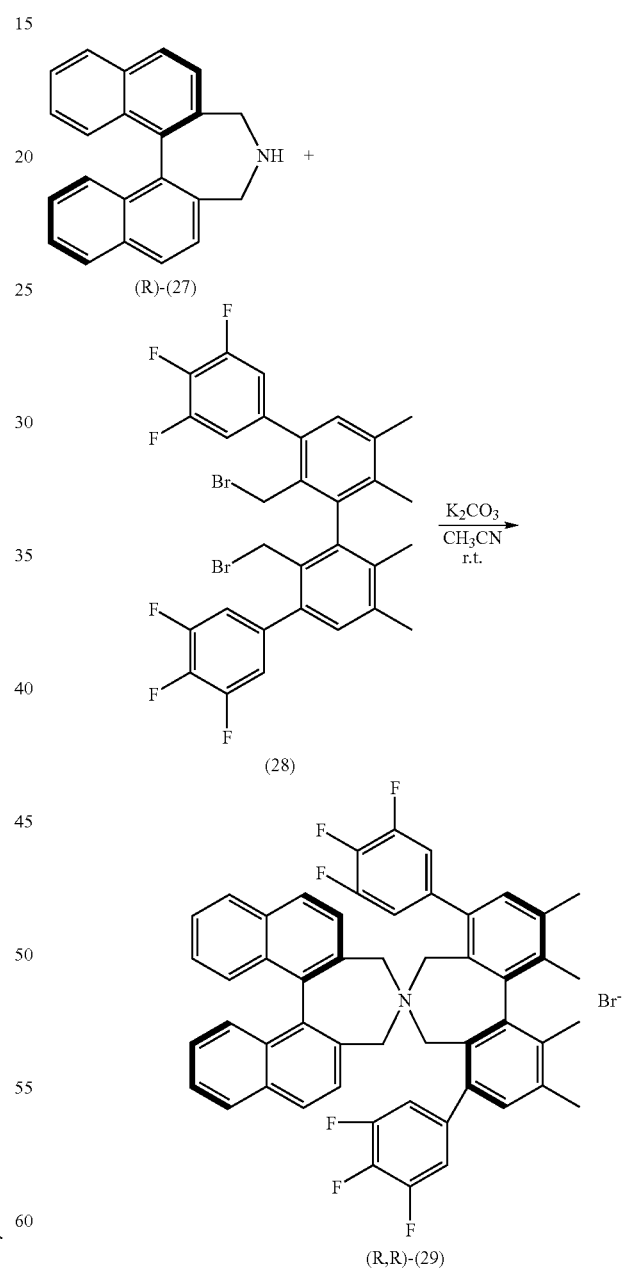

Under the presence of 140 mg of potassium carbonate, 56 mg of a chiral secondary amine (27) and 80 mg of racemic dibromomethylbiphenyl (28), which was 2.1 equivalent of said amine, were stirred in an acetonitrile solvent at room temperature for 12 hours as in Example 1. After the completion of the reaction, the resultant was purified by extraction/column chromatography (methylene chloride:methanol=10:1) to obtain 82 mg of an optically pure compound (R,R)-(29) (yield was 94%), $[\alpha]_D^{23}=-120.2°$ (c1.0, CHCl$_3$)

$^1$H NMR (300 MHz, CDCl$_3$), δ7.92 (2H, d, J=8.4 Hz, ArH), 7.20-7.57 (12H, m, ArH), 7.11 (2H, d, J=8.4 Hz, ArH), 6.32 (2H, d, J=8.7 Hz, ArH), 4.55 (2H, d, J=13.8 Hz, ArCH$_2$), 4.47 (4H, d, J=14.1 Hz, ArCH$_2$), 4.18 (2H, d, J=14.1 Hz, ArCH$_2$), 3.61 (2H, d, J=12.9 Hz, ArCH$_2$), 2.45 (6H, s, ArCH$_3$), 2.05 (6H, s, ArCH$_3$)

Example 5

Production of Optically Active Quaternary Ammonium Salt Compound (45)

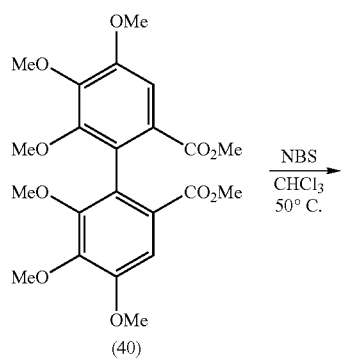

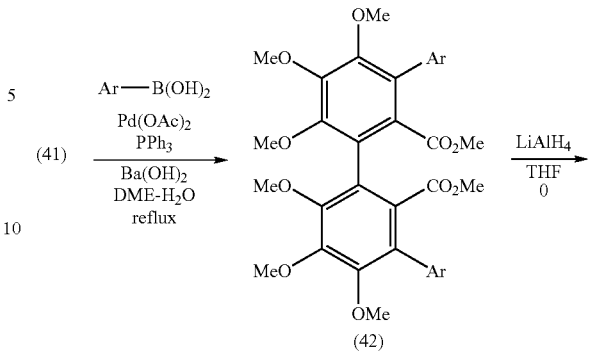

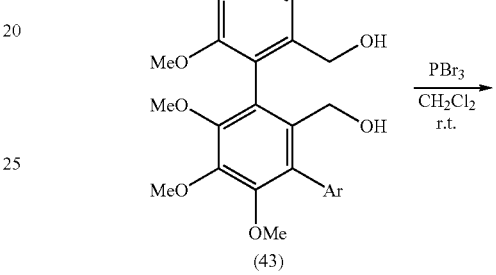

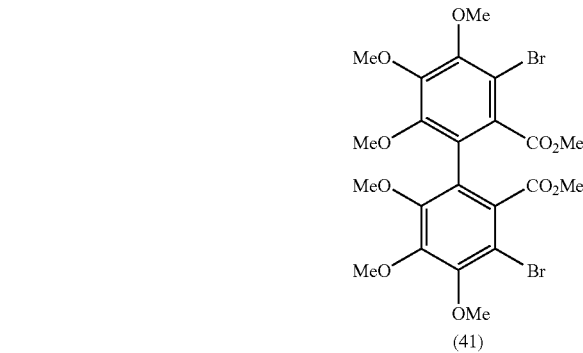

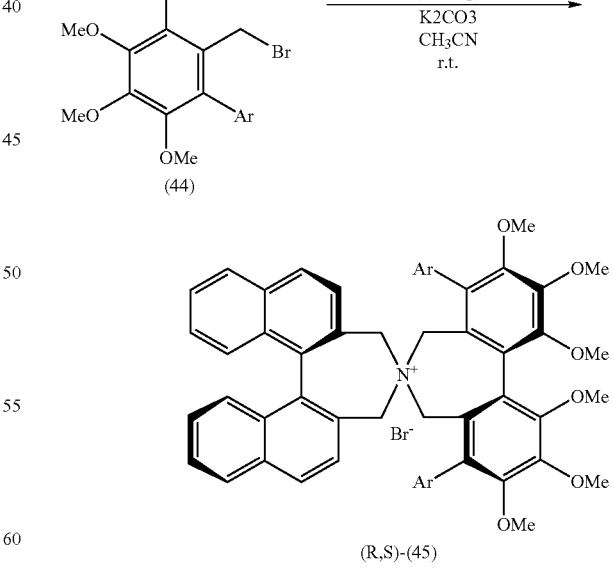

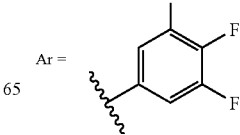

1.97 g (4.37 mmol) of a compound (40) and 2.33 g (13.1 mmol) of N-bromosuccinimide were reacted in 20 ml of a chloroform solvent at room temperature for 12 hours. After the completion of the reaction, the resultant was extracted with ethyl acetate, dried/concentrated, and thereafter purified by column chromatography (ethyl acetate:hexane=1:3) to obtain a compound (41) (yield was 94%).

$^1$H NMR (300 MHz, CDCl$_3$), δ3.96 (6H, s, ArCO$_2$CH$_3$), 3.94 (6H, s, ArOCH$_3$), 3.79 (6H, s, ArOCH$_3$), 3.94 (6H, s, ArOCH$_3$)

The compounds (41) to (45) were synthesized according to the methods of Reference Example 7, and Examples 1 and 4.

Compound (42) (yield was 80%)

¹H NMR (300 MHz, CDCl₃), δ6.90-6.95 (4H, m, ArH), 3.98 (6H, s, ArCO₂CH₃), 3.85 (6H, s, ArOCH₃), 3.70 (6H, s, ArOCH₃), 3.27 (6H, s, ArOCH₃)

Compound (44) (yield was 81% from the compound (42))

¹H NMR (300 MHz, CDCl₃), δ6.95-7.15 (4H, min, ArH), 3.90-4.00 (4H, m, ArCH₂O—), 3.95 (6H, s, ArOCH₃), 3.87 (6H, s, ArOCH₃), 3.73 (6H, s, ArOCH₃)

Compound (45) (yield was 83%)

[α]$_D^{22}$=89.55° (c0.22, CHCl₃)

¹H NMR (300 MHz, CDCl₃), δ6.75-8.00 (12H, m, ArH), 6.47 (4H, d, J=8.4 Hz, ArH), 4.65 (2H, d, J=14.1 Hz ArCH₂), 4.44 (2H, d, J=12.6 Hz, ArCH₂), 4.40 (2H, d, J=13.5 Hz, ArCH₂), 4.11 (6H, s, ArOCH₃), 3.91 (6H, s, ArOCH₃), 3.75 (6H, s, ArOCH₃), 3.61 (2H, d, J=13.8 Hz, ArCH₂)

Example 6

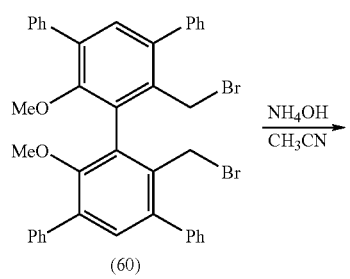

(60)

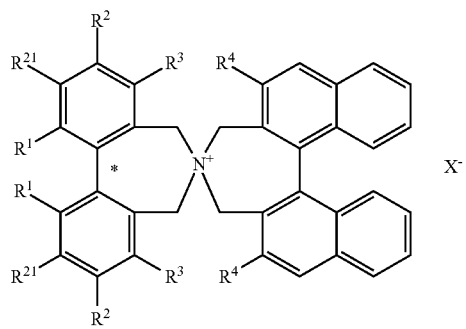

(61)

Production of Amine (61)

30 mg (0.043 mmol) of a compound (60) was dissolved in 2 ml of acetonitrile, and 0.1 to 0.2 ml of 25% ammonia water solution was added dropwise thereto. The reaction mixture was stirred at room temperature for 48 hours, concentrated to remove the solvent, and extracted with ethyl acetate. The resultant was subjected to drying/concentration and thereafter purified by column chromatography (methylene chloride: methanol=15:1) to obtain 20 mg (0.036 mmol) of a targeted substance (61) (yield was 84%).

The compounds of the present invention including those obtained in the abovementioned Examples are described in Tables 1 to 4.

TABLE 1

Optically active quaternary ammonium salt (1)

| Compound No. | $R^1$ | $R^2$ | $R^{21}$ | $R^3$ | $R^4$ | X | Physical property value (¹HNMR, 300 MHz, CDCl₃) | Physical property (angle of rotation) | Note |
|---|---|---|---|---|---|---|---|---|---|
| 26 | Me | H | Me | H | 3,4,5-F₃—C₆H₂ | Br | δ8.21 (2H, s, ArH), 8.08 (2H, d, J = 8.4 Hz, ArH), 7.205-7.60 (8H, m, ArH), 7.09 (2H, d, J = 8.7 Hz, ArH), 6.71 (2H, d, J = 7.8 Hz, ArH), 6.02 (2H, d, J = 7.8 Hz, ArH), 4.71 (2H, d, J = 13.8 Hz, ArCH₂), 4.50 (2H, d, J = 14.1 Hz, ArCH₃), 4.04 (2H, d, J = 13.5 Hz, ArCH₃), 3.49 (2H, d, J = 13.2 Hz, ArCH₂), 2.30 (6H, s, ArCH₃), 1.88 (6H, s, ArCH₂) | [α]$_D^{22}$ = +25.6° (c1.0, CHCl₃) | S,S-form |

TABLE 1-continued

Optically active quaternary ammonium salt (1)

| Compound No. | R¹ | R² | R²¹ | R³ | R⁴ | X | Physical property value ($^1$HNMR, 300 MHz, CDCl₃) | Physical property (angle of rotation) | Note |
|---|---|---|---|---|---|---|---|---|---|
| 29 | Me | H | Me | 3,4,5-F₃—C₆H₂ | H | Br | δ7.92 (2H, d, J = 8.4 Hz, ArH), 7.20-7.57 (12H, m, ArH), 7.11 (2H, d, J = 8.4 Hz, ArH), 6.32 (2H, d, J = 8.7 Hz, ArH), 4.55 (2H, d, J = 13.8 Hz, ArCH₂), 4.47 (4H, d, J = 14.1 Hz, ArCH₂), 4.18 (2H, d, J = 14.1 Hz, ArCH₂)₂ 3.61 (2H, d, J = 12.9 Hz, ArCH₂), 2.45 (6H, s, ArCH₃), 2.05 (6H, s, ArCH₃) | $[\alpha]_D^{23}$ = −120.2° (c1.0, CHCl₃) | R,R-form |
| 30 | Me | H | Me | H | 3,5-(CF₃)₂—C₆H₂ | Br | δ8.27 (2H, s, ArH), 7.35-8.16 (12H, m, ArH), 7.16 (2H, d, J = 8.7 Hz, ArH), 6.43 (2H, d, J = 7.8 Hz, ArH), 5.73 (2H, d, J = 7.8 Hz, ArH), 4.71 (2H, d, J = 14.1 Hz, ArCH₃), 4.53 (2H, d, J = 13.8 Hz, ArCH₂), 4.10 (2H, d, J = 13.5 Hz, ArCH₂), 3.42 (2H, d, J = 12.9 Hz, ArCH₂), 2.20 (6H, s, ArCH₃), 1.82 (6H, s, ArCH₃) | $[\alpha]_D^{22}$ = +25.6° (c1.0, CHCl₃) | S,S-form |
| 31 | Me | H | Me | H | 3,4,5-F₃—C₆H₂ | Br | δ8.22 (2H, s, ArH), 8.08 (2H, d, J = 8.4 Hz, ArH), 7.64 (2H, d, J = 7.2 Hz, ArH), 6.91-7.60 (12H, m, ArH), 5.90 (2H, d, J = 7.5 Hz, ArH), 4.85 (2H, d, J = 14.1 Hz, ArCH₂), 4.57 (2H, d, J = 13.5 Hz, ArCH₂), 4.11 (2H, d, J = 13.5 Hz, ArCH₂), 3.76 (6H, s, OCH₃), 3.61 (2H, d, J = 12.9 Hz, ArCH₂) | $[\alpha]_D^{23}$ = +18.0° (c0.15, CHCl₃) | S,R-form |
| 45 | OMe | OMe | OMe | 3,4,5-F₃—C₆H₂ | H | Br | δ6.75-8.00 (12H, m, ArH), 6.47 (4H, d, J = 8.4 Hz, ArH), 4.65 (2H, d, J = 14.1 Hz, ArCH₂), 4.44 (2H, d, J = 12.6 Hz, ArCH₂), 4.40 (2H, d, J = 13.5 Hz, ArCH₂), 4.11 (6H, s, ArOCH₃), 3.91 (6H, s, ArOCH₃), 3.75 (6H, s, ArOCH₃), 3.61 (2H, d, J = 13.8 Hz, ArCH₂) | $[\alpha]_D^{22}$ = −89.55° (c0.22, CHCl₃) | R,S-form |
| 46 | OMe | OMe | OMe | H | 3,5-(CF₃)₂—C₆H₂ | Br | δ8.76 (2H, s, ArH), 8.17 (2H, s, ArH), 7.01-7.92 (12H, m, ArH), 6.11 (2H, d, J = 8.4 Hz, ArH), 2.25-4.80 (8H, m, ArCH₂), 4.14 (4H, s, ArOCH₃, homo), 4.09 (2H, s, ArOCH₃, hetero), 4.07 (2H, s, ArOCH₃, hetero), 3.98 (4H, s, ArOCH₃, homo), 3.81 (2H, s, ArOCH₃, hetero), 3.76 (4H, s, ArOCH₃, homo) | $[\alpha]_D^{22}$ = −63.125° (c0.48, CHCl₃) | Mixture of R,S-form and R,R-form (ratio is 2:1) |
| 47 | OMe | H | C₆H₅ | C₆H₅ | H | Br | δ7.08-7.85 (32H, m, ArH), 6.15 (2H, d, J = 8.4 Hz, ArH), 4.86 (2H, d, J = 13.8 Hz, ArCH₂), 4.69 (2H, d, J = 13.5 Hz, ArCH₂), 4.38 (2H, d, J = 13.2 Hz, ArCH₂), 3.69 (2H, d, J = 13.2 Hz, ArCH₂), 3.43 (6H, s, ArCH₃) | | |
| 48 | OMe | H | 4-CF₃—C₆H₄ | 4-CF₃—C₆H₄ | H | Br | δ7.07-7.95 (28H, m, ArH), 6.11 (2H, d, J = 8.4 Hz, ArH), 4.90 (2H, d, J = 12.0 Hz, ArCH₂), 4.74 (2H, d, J = 13.8 Hz, ArCH₂), 4.46 (2H, d, J = 14.7 Hz, ArCH₂), 3.69 (2H, d, J = 13.8 Hz, ArCH₂), 3.44 (6H, s, ArOCH₃) | | |
| 49 | OMe | H | 4-F—C₆H₄ | 4-F—C₆H₄ | H | Br | 7.60-7.65 (4H, m, ArH), 7.40-7.55 (4H, m, ArH), 7.28 (2H, s, ArH), 7.05-7.20 (8H, m, ArH), 4.27 (4H, s, ArCH₂), 3.35 (6H, s, ArOCH₃) | | |

TABLE 1-continued

Optically active quaternary ammonium salt (1)

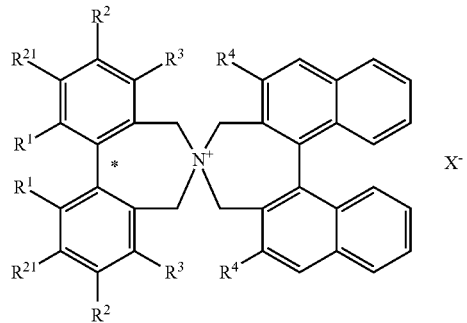

| Compound No. | $R^1$ | $R^2$ | $R^{21}$ | $R^3$ | $R^4$ | X | Physical property value ($^1$HNMR, 300 MHz, CDCl$_3$) | Physical property (angle of rotation) | Note |
|---|---|---|---|---|---|---|---|---|---|
| 50 | OMe | H | 3-CF$_3$—C$_6$H$_4$ | 3-CF$_3$—C$_6$H$_4$ | H | Br | δ7.02-7.98 (28H, m, ArH), 6.14 (2H, br, ArH), 4.71 (2H, d, J = 13.2 Hz, ArCH$_2$), 3.40-3.77 (6H, m, ArCH$_2$), 3.55 (6H, s, ArOCH$_3$) | | |
| 51 | OMe | H | 3,5-CF$_3$—C$_6$H$_3$ | 3,5-CF$_3$—C$_6$H$_3$ | H | Br | δ7.05-8.22 (24H, m, ArH), 6.00 (2H, d, J = 8.4 Hz, ArH), 5.11 (2H, br, ArCH$_2$), 4.51-4.60 (4H, m, ArCH$_2$), 3.73 (2H, d, J = 13.2 Hz, ArCH$_2$), 3.52 (6H, s, ArOCH$_3$) | | |
| 52 | OMe | OMe | H | 3,5-CF$_3$—C$_6$H$_3$ | H | Br | δ8.75 (2H, s, ArH), 8.10 (2H, s, ArH), 6.85-7.93 (14H, m, ArH), 6.22 (2H, d, J = 8.4 Hz, ArH), 4.55 (2H, d, J = 13.5 Hz, ArCH$_2$), 4.43 (2H, d, J = 13.5 Hz, ArCH$_2$), 4.31 (2H, d, J = 13.5 Hz, ArCH$_2$), 3.99 (12H, s, ArOCH$_3$), 3.58 (2H, d, J = 13.5 Hz, ArCH$_2$) | | |
| 53 | OMe | H | OMe | 3,5-CF$_3$—C$_6$H$_3$ | H | Br | δ8.22 (2H, s, ArH), 6.98-7.95 (16H, m, ArH), 5.95 (2H, d, J = 8.4 Hz, ArH), 4.66 (2H, d, J = 12.9 Hz, ArCH$_2$), 4.32-4.42 (4H, m, ArCH$_2$), 4.11 (6H, s, ArOCH$_3$), 3.94 (6H, s, ArOCH$_3$), 3.57 (2H, d, J = 13.5 Hz, ArCH$_2$) | | |
| 54 | OMe | H | H | 3,5-CF$_3$—C$_6$H$_3$ | H | Br | δ8.18 (2H, s, ArH), 7.03-7.95 (18H, m, ArH), 6.04 (2H, d, J = 8.4 Hz, ArH), 4.66 (2H, d, J = 14.1 Hz, ArCH$_2$), 4.50 (2H, d, J = 13.5 Hz, ArCH$_2$), 4.45 (2H, d, J = 13.8 Hz, ArCH$_2$), 3.94 (6H, s, ArOCH$_3$), 3.63 (2H, d, J = 13.2 Hz, ArCH$_2$) | | |
| 55 | OMe | H | H | 3,4,5-F$_3$—C$_6$H$_2$ | H | Br | δ7.92 (2H, d, J = 8.4 Hz, ArH), 7.09-7.65 (16H, m, ArH), 6.35 (2H, d, J = 8.4 Hz, ArH), 4.62 (2H, d, J = 13.8 Hz, ArCH$_2$), 4.45-4.52 (4H, m, ArCH$_2$), 3.89 (6H, s, ArOCH$_3$), 3.68 (2H, d, J = 13.5 Hz, ArCH$_2$) | | |
| 56 | OMe | OMe | OMe | 3,5-CF$_3$—C$_6$H$_3$ | H | | δ6.75-8.00 (12H, m, ArH), 6.47 (4H, d, J = 8.4 Hz, ArH), 4.65 (2H, d, J = 14.1 Hz, ArCH$_2$), 4.44 (2H, d, J = 12.6 Hz, ArCH$_2$), 4.40 (2H, d, J = 13.5 Hz, ArCH$_2$), 4.11 (6H, s, ArOCH$_3$), 3.91 (6H, s, ArOCH$_3$), 3.75 (6H, s, ArOCH$_3$), 3.61 (2H, d, J = 13.8 Hz, ArCH$_2$) | $[α]_D^{22}$ = −89.55° (c0.22, CHCl$_3$) | |
| 57 | Me | Me | H | 3,4,5-F$_3$—C$_6$H$_2$ | H | | δ7.92 (2H, d, J = 8.4 Hz, ArH), 7.20-7.57 (12H, m, ArH), 7.11 (2H, d,d J = 8.4 Hz, ArH), 6.32 (2H, d, J = 8.7 Hz, ArH), 4.55 (2H, d, J = 13.8 Hz, ArCH$_2$), 4.47 (4H, d, J = 14.1 Hz, ArCH$_2$), 4.18 (2H, d, J = 14.1 Hz, ArCH$_2$), 3.61 (2H, d, J = 12.9 Hz, ArCH$_2$), 2.45 (6H, s, ArCH$_3$), 2.05 (6H, s, ArCH$_3$) | | |

TABLE 2

Optically active quaternary ammonium salt (1)

| Compound No. | R¹ | R² | R²¹ | R³ | R⁴ | R⁵ | R⁶ | X | Physical property value (¹HNMR, 300 MHz, CDCl₃) | Physical property (angle of rotaion) | Note |
|---|---|---|---|---|---|---|---|---|---|---|---|
| 32 | Me | H | Me | 3,4,5-F₃—C₆H₂ | H | H | OMe | Br | δ7.41 (4H, s, ArH), 7.00 (2H, d, J = 8.7 Hz, ArH), 6.85-6.91 (4H, m, ArH), 5.70 (2H, d, J = 6.9 Hz, ArH), 4.56 (2H, d, J = 14.1 Hz, ArCH₂), 4.40 (2H, d, J = 13.2 Hz, ArCH₂), 3.86 (2H, d, J = 13.5 Hz, ArCH₂), 3.75 (6H, s, OCH₃), 3.45 (2H, d, J = 12.9 Hz, ArCH₂), 2.48 (6H, s, ArCH₃), 2.04 (6H, s, ArCH₃) | | |

TABLE 3

| Compound No. | R¹ | R² | R²¹ | R³ | Y² | Physical property value (¹HNMR, 300 MHz, CDCl₃) |
|---|---|---|---|---|---|---|
| 22 | Me | H | Me | 3,4,5-F₃—C₆H₂ | Br | δ7.15 (2H, d, J = 6.6 Hz, ArH), 7.12 (2H, d, J = 6.6 Hz, ArH), 7.09 (2H, s, ArH), 4.03 (4H, d, J = 2.4 Hz, ArCH₂), 2.37 (6H s, ArCH₃), 1.97 (6H, s, ArCH₃) |
| 44 | OMe | OMe | OMe | 3,4,5-F₃—C₆H₂ | Br | δ6.95-7.15 (4H, m, ArH), 3.90-4.00 (4H m, ArCH₂O—), 3.95 (6H, s, ArOCH₃), 3.87 (6H, s, ArOCH₃), 3.73 (6H, s, ArOCH₃) |
| 47B | OMe | H | C₆H₅ | C₆H₅ | Br | δ7.30-7.68 (22H, m, ArH), 4.34 (4H, d, J = 2.1 Hz, ArCH₂), 3.37 (6H, s, ArOCH₃) |

TABLE 3-continued

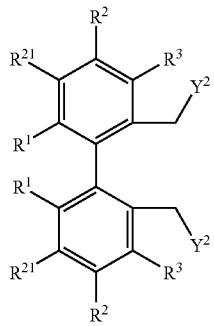

| Compound No. | $R^1$ | $R^2$ | $R^{21}$ | $R^3$ | $Y^2$ | Physical property value ($^1$HNMR, 300 MHz, CDCl$_3$) |
|---|---|---|---|---|---|---|
| 48B | OMe | H | 4-CF$_3$—C$_6$H$_4$ | 4-CF$_3$—C$_6$H$_4$ | Br | δ7.60-7.78 (16H, m, ArH), 7.34 (2H, s, ArH), 4.27 (4H, s, ArCH$_2$), 3.38 (6H, s, ArOCH$_3$) |
| 49B | OMe | H | 4-F—C$_6$H$_4$ | 4-F—C$_6$H$_4$ | Br | δ7.60-7.78(16H, m, ArH), 7.34 (2H, s, ArH), 4.27 (4H, s, ArCH$_2$), 3.38 (6H, s, ArOCH$_3$) |
| 50B | OMe | H | 3-CF$_3$—C$_6$H$_4$ | 3-CF$_3$—C$_4$H$_4$ | Br | δ7.55-7.93 (16H, m, ArH), 7.35 (2H, s, ArH), 4.25 (4H, s, ArCH$_2$), 3.37 (6H, s, ArOCH$_3$) |
| 51B | OMe | H | 3,5-CF$_3$—C$_6$H$_3$ | 3-CF$_3$—C$_6$H$_4$ | Br | δ7.90-8.15 (12H, m, ArH), 7.39 (2H, s, ArH), 4.17 (4H, s, ArCH$_2$), 3.41 (6H, s, ArOCH$_3$) |
| 52B | OMe | OMe | H | 3,5-CF$_3$—C$_6$H$_3$ | Br | δ7.81-7.92 (6H, m, ArH), 6.65 (2H, s, ArH), 3.81-3.92 (4H, m, ArCH$_2$), 3.83 (6H, s, ArOCH$_3$), 3.79 (6H, s, ArOCH$_3$) |
| 53B | OMe | H | OMe | 3,5-CF$_3$—C$_6$H$_3$ | Br | δ8.02 (4H, s, ArH), 7.94 (2H, s, ArH), 6.87 (2H, s, ArH), 4.04 (4H, s, ArCH$_2$), 3.95 (6H, s, ArOCH$_3$), 3.86 (6H, s, ArOCH$_3$) |
| 54B | OMe | H | H | 3,5-CF$_3$—C$_6$H$_3$ | Br | δ8.01 (4H, s, ArH), 7.91 (2H, s, ArH), 7.32 (2H, d, J = 8.4 Hz, ArH) 7.08 (2H, d, J = 8.4 Hz, ArH), 4.02 (4H, d, J = 3.0 Hz, ArCH$_2$), 3.80 (6H, s, ArOCH$_3$) |
| 55B | OMe | H | H | 3,4,5-F$_3$—C$_6$H$_2$ | Br | δ7.26 (2H, d, J = 8.4 Hz, ArH), 7.03 (2H, d, J = 8.4 Hz, ArH), 7.10-7.17 (4H, m, ArH), 4.06 (4H, s, ArCH$_2$), 3.77 (6H, s, ArOCH$_3$) |
| 56B | OMe | OMe | OMe | 3,5-CF$_3$—C$_6$H$_3$ | Br | δ6.95-7.15 (4H, m, ArH), 3.90-4.00 (4H, m, ArCH$_2$O—), 3.95 (6H, s, ArOMe), 3.87 (6H, s, ArOMe), 3.73 (6H, s, ArOMe) |
| 57B | Me | Me | H | 3,4,5-F$_3$—C$_6$H$_2$ | Br | δ7.15 (2H, d, J = 6.6 Hz, ArH), 7.12 (2H, d, J = 6.6 Hz, ArH), 7.09 (2H, s, ArH), 4.03 (4H, d, J = 2.4 Hz, ArCH$_2$), 2.37 (6H, s, ArCH$_3$), 1.97 (6H, s, ArCH$_3$) |

TABLE 4

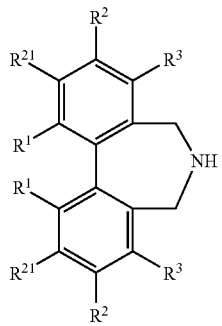

| Compound No. | R¹ | R² | R²¹ | R³ | Physical property value (¹HNMR, 300 MHz, CDCl₃) |
|---|---|---|---|---|---|
| 23 | Me | H | Me | 3,4,5-F₃—C₆H₂ | δ7.31 (2H, s, ArH), 7.24 (2H, d, J = 6.6 Hz, ArH), 7.21 (2H, d, J = 6.6 Hz, ArH), 4.14 (2H, d, J = 13.8 Hz, ArCH₂), 3.46 (2H, d, J = 13.8 Hz, ArCH₂), 2.43 (6H, s, ArCH₃), 2.09 (6H, s, ArCH₃) |
| 47A | OMe | H | C₆H₅ | C₆H₅ | δ7.33-7.69 (22H, m, ArH), 3.95 (4H, d, J = 12.6 Hz, ArCH₂), 3.41 (4H, d, J = 12.6 Hz, ArCH₂), 3.29 (6H, s, ArOCH₃) |
| 48A | OMe | H | H | 3,5-CF₃—C₆H₃ | δ7.96 (4H s, ArH), 7.85 (2H, s, ArH), 7.38 (2H, d, J = 8.4 Hz, ArH), 7.08 (2H, d, J = 8.4 Hz, ArH), 3.91 (6H, s, ArOCH₃), 3.72 (2H, d, J = 12.9 Hz, ArCH₂), 3.34 (2H, d, J = 12.9 Hz, ArCH) |
| 56A | OMe | OMe | OMe | 3,5-CF₃—C₆H₃ | δ8.32 (2H, s, ArH), 7.76 (2H, s, ArH), 7.63 (2H, s, ArH), 3.98 (6H, s, ArOCH₃), 3.87 (6H, s, ArOCH₃), 3.67 (6H, s, ArOCH₃), 3.45-3.76 (4H, m, ArCH₂); m.p. = 258-260° (decomp. |
| 57A | Me | H | Me | 3,4,5-CF₃—C₆H₂ | δ7.00-7.22 (6H, m, ArH), 3.72 (2H, d, J = 12.6 Hz, ArCH₂), 3.10 (2H, d, J = 12.6 Hz, ArCH₂), 2.37 (6H, s, ArCH₃), 2,06 (6H, s, ArCH₃) |

Reference Example 1

Asymmetric Synthesis of α-Amino Acid Using Optically Active Quaternary Ammonium Salt Compound (29)

74 mg of tert-butyl(benzhydrylideneamino)acetate, 2.0 mg of an optically active quaternary ammonium salt compound (R,R)-(29), and 36 µl of benzylbromide were added to 2 ml of a toluene solvent at 0° C. 0.5 ml of 50% KOH aqueous solution was added dropwise to the resulting solution while stirring. The reaction solution was stirred for 8 hours at 0° C. and thereafter extracted by adding water and ether. The reaction product was purified by column chromatography (hexane:ether=15:1) to obtain targeted tert-butyl-2-(benzhydrylideneamino)-3-phenylpropionate (yield was 95%).

Furthermore, optical purity was determined by HPLC analysis (hexane:isopropyl alcohol=100:1) using CHIRAL-CEL® OD manufactured by Daicel Chemical Industries, Ltd (asymmetric yield was 97% ee).

Reference Example 2

Asymmetric Synthesis of α-Amino Acid Using Optically Active Quaternary Ammonium Salt Compound (45)

When the same reaction as in the above Reference Example 1 was carried out using the catalyst represented by the formula (45), a corresponding alkylated substance was obtained with a yield of 96% and asymmetric yield of 94% ee.

Reference Example 3

Asymmetric Synthesis of α-Amino Acid Using Optically Active Quaternary Ammonium Salt Compound (46)

When the same reaction as in the above Reference Example 1 was carried out using the catalyst represented by the formula (46), a corresponding alkylated substance was obtained with a yield of 100% and asymmetric yield of 98% ee.

Reference Example 4

Production of 2,3,2',3'-tetramethyl-6,6'-dinitrobiphenyl (34)

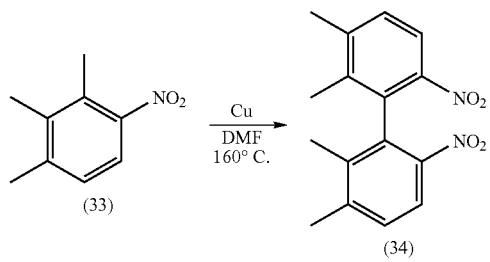

In 20 ml of a DMF solvent, 5.5 g (20 mmol) of 2-iodo-3,4-dimethyl-1-nitrobenzene and 10 g (155 mmol) of copper powder were heated at 150° C. for 48 hours. After the completion of the reaction, copper powder was removed by filtration and thereafter, the resultant was extracted using ethyl acetate, dried/concentrated, and then purified by column chromatography (ethyl acetate:hexane=1:10) to obtain 2.9 g (0.96 mmol) of 2,3,2',3'-tetramethyl-6,6'-dinitrobiphenyl (34) (yield was 96%).

$^1$H NMR (300 MHz, CDCl$_3$), δ7.91 (2H, d, J=8.4 Hz, ArCH), 7.34 (2H, d, J=8.4 Hz, ArCH), 2.40 (6H, s, ArCH$_3$), 1.84 (6H, s, ArCH$_3$)

Reference Example 5

Production of 5,6,5',6'-tetramethylbiphenyl-2,2'-diamine (35)

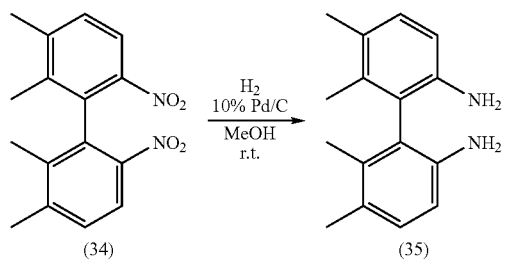 [SMILES: Cc1ccc([N+](=O)[O-])c(-c2c([N+](=O)[O-])ccc(C)c2C)c1C ; Cc1ccc(N)c(-c2c(N)ccc(C)c2C)c1C]

3.0 g (10 mmol) of the compound (34) and 500 mg (5 mol %) of 10% Pd/C were added to 50 ml of a methanol solvent and were stirred for 12 hours under hydrogen atmosphere. After the completion of the reaction, solid matter was removed by filtration and thereafter, the resultant was purified by column chromatography (ethyl acetate:hexane=1:5) to obtain 2.4 g (10 mmol) of 5,6,5',6'-tetramethylbiphenyl-2,2'-diamine (35) (yield was 100%).

$^1$H NMR (300 MHz, CDCl$_3$), δ6.97 (2H, d, J=8.1 Hz, ArH), 6.58 (2H, d, J=8.4 Hz, ArH), 3.25 (4H, br, NH$_2$), 2.21 (6H, s, ArCH$_3$), 1.86 (6H, s, ArCH$_3$)

Reference Example 6

Production of 3,3'-dibromo-5,6,5',6'-tetramethylbiphenyl-2,2'-diamine (36)

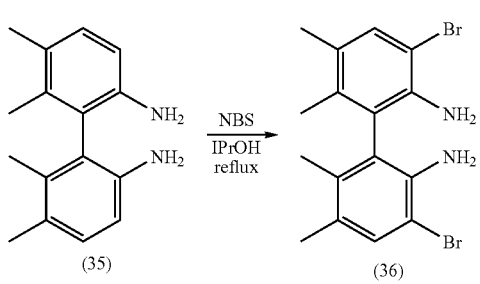

After dissolving 2.75 g (11.5 mmol) of the compound (35) in 20 ml of isopropyl alcohol, 4.45 g (25 mmol) of NBS was added thereto at 60° C. The reaction mixture was stirred for 1 hour under reflux and thereafter, poured into ice-cold water to stop the reaction. The obtained suspension was extracted with ethyl acetate and the resultant was dried/concentrated and thereafter purified by column chromatography (ethyl acetate:hexane=1:10) to obtain 2.98 g (7.48 mmol) of 3,3'-dibromo-5,6,5',6'-tetzamethylbiphenyl-2,2'-diamine (36) (yield was 65%).

$^1$H NMR (300 MHz, CDCl$_3$), δ7.27 (2H, s, ArH), 3.71 (4H, br, NH$_2$), 2.21 (6H, s, ArCH$_3$), 1.80 (6H, s, ArCH$_3$)

Reference Example 7

3,4,5,3''',4''',5'''-hexafluoro-4',5',4'',5''-tetramethyl-(1,1';3',3'';1'',1''')quaterphenyl-2',2''-diamine (37)

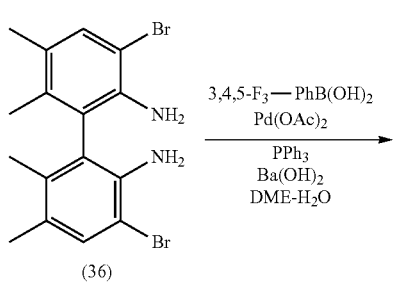

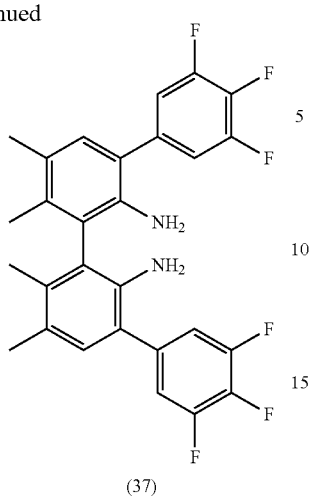

(37)

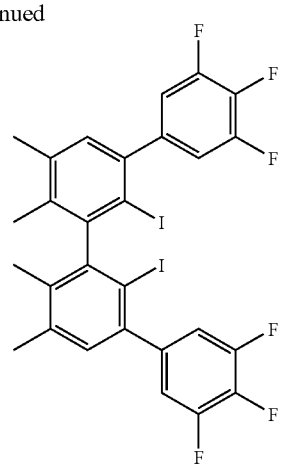

(38)

1.5 g (3.77 mmol) of the compound (36), 1.5 g (9.0 mmol) of 3,4,5-trifluorophenylborate, 42 mg (5 mol %) of Pd(OAc)$_2$, 99 mg (10 mol %) of PPh$_3$, and 3.78 g (12.0 mmol) of Ba(OH)$_2$·8H$_2$O were added to 10 ml of a DME-H$_2$O (9:1 (v/v)) solvent and were stirred for 12 hours at 100° C. under argon atmosphere. After the completion of the reaction, the obtained reaction mixture was poured into a saturated NH$_4$Cl solution and thereafter, the catalyst was removed by celite filtration. Furthermore, the resulting solution was extracted with ethyl acetate, dried/concentrated, and then purified by column chromatography (ethyl acetate:hexane=1:10) to obtain 1.63 g (3.21 mmol) of the compound (37) (yield was 85%).

$^1$H NMR (300 MHz, CDCl$_3$), δ7.15 (2H, d, J=6.6 Hz, ArH), 7.12 (2H, d, J=6.6 Hz, ArH), 6.92 (2H, s, ArH), 3.46 (4H, br, NH$_2$), 2.26 (6H, s, ArCH$_3$), 1.92 (6H, s, ArCH$_3$)

Reference Example 8

Production of 2',2''-diiodo-3,4,5,3''',4''',5'''-hexafluoro-4',5',4'',5''-tetramethyl-(1,1';3,3'';1'',1''')quaterphenyl (38)

760 mg (1.52 mmol) of the compound (37) was dissolved in 20 ml of 6M HCl and the resulting solution was cooled down to 0° C. 315 mg (4.56 mmol) of NaNO$_2$ aqueous solution was slowly added dropwise to this solution in 5 minutes. Furthermore, 1.51 g (9.12 mmol) of KI aqueous solution was added dropwise thereto at the same temperature and the reaction temperature was increased to 80° C. after the addition. After stirring the reaction mixture for another 2 hours at the same temperature, it was cooled using ice-cold water and the reaction was stopped by adding sodium sulfite thereto. The obtained mixture was extracted with diethylether and the resultant was dried/concentrated and thereafter purified by column chromatography (ethyl acetate:hexane=1:10) to obtain 1.03 g (1.43 mmol) of the compound (38) (yield was 94%).

$^1$H NMR (300 MHz, CDCl$_3$), δ7.09 (2H, s, ArH), 6.99 (2H, d, J=7.2 Hz, ArH), 6.97 (2H, d, J=6.6 Hz, ArH), 2.33 (6H, s, ArCH$_3$), 1.99 (6H, s, ArCH$_3$)

Reference Example 9

Production of 3,4,5,3''',4''',5'''-hexafluoro-4,5',4'',5''-tetramethyl-(1,1';3',3'';1'',1''')quaterphenyl-2',2''-dimethyl dicarbonate (20)

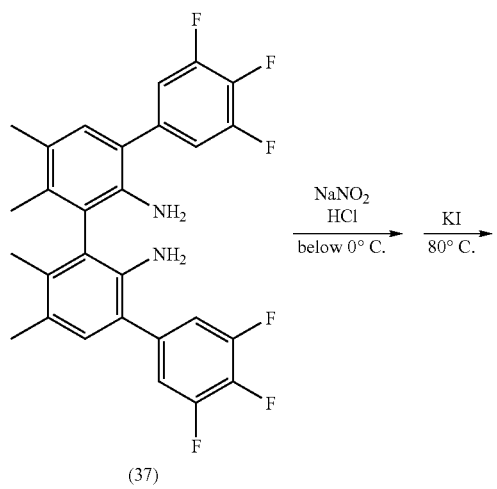

(37)

NaNO$_2$
HCl
below 0° C.

KI
80° C.

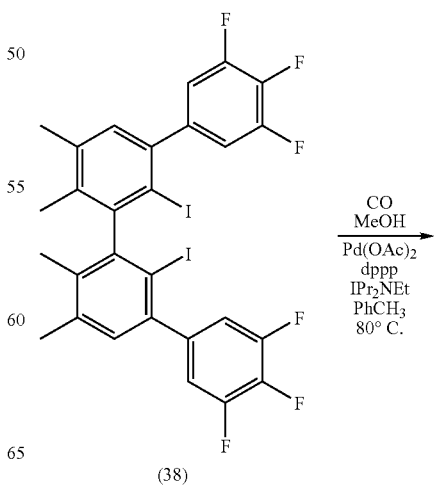

(38)

CO
MeOH
Pd(OAc)$_2$
dppp
IPr$_2$NEt
PhCH$_3$
80° C.

-continued

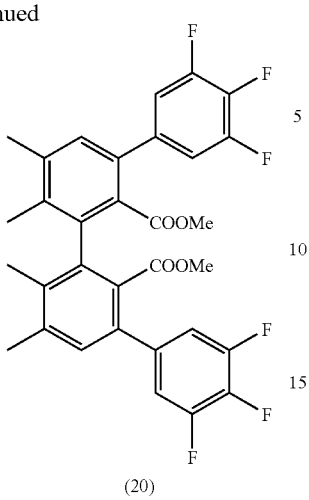

(20)

361 mg (0.5 mmol) of the compound (38), 5.6 mg (5 mol %) of Pd(OAc)$_2$, 10.3 mg (5 mol %) of 1,3-bis(diphenylphosphino)propane, 0.52 ml (3 mmol) of N-ethyldiisopropylamine, and 3 ml of MeOH were added to 3 ml of a toluene solvent and were stirred for 48 hours at 80° C. under 10 atm of carbon monoxide. After the completion of the reaction, the catalyst was removed by filtration and thereafter, the resultant was purified by column chromatography (ethyl acetate:hexane=1:20) to obtain 198 mg (0.34 mmol) of the compound (20) (yield was 68%).

$^1$H NMR (300 MHz, CDCl$_3$), δ7.14 (2H, s, ArH), 6.99 (2H, d, J=6.6 Hz, ArH), 6.94 (2H, d, J=6.3 Hz, ArH), 3.27 (6H, s, ArH), 2.40 (6H, s, ArCH$_3$), 1.97 (6H, s, ArCH$_3$)

The invention claimed is:
1. An optically active quaternary ammonium salt compound represented by formula (1)

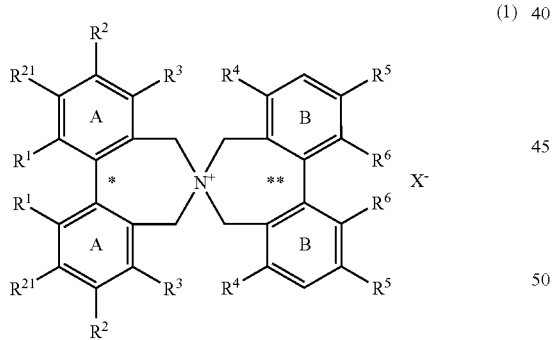

(1)

wherein $R^1$ represents a halogen, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{3-8}$ heteroaryl which is optionally substituted, a $C_{1-8}$ alkoxy which is optionally substituted and which is linear, branched, or cyclic, or a $C_{7-16}$ aralkyl which is optionally substituted;

$R^2$ and $R^{21}$ each independently represents hydrogen, halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, or a $C_{7-16}$ aralkyl which is optionally substituted;

$R^3$ and $R^4$ each independently represents hydrogen, a $C_{6-14}$ aryl which is optionally substituted, a $C_{3-8}$ heteroaryl which is optionally substituted, or a $C_{7-16}$ aralkyl which is optionally substituted, with a proviso that $R^3$ and $R^4$ are not hydrogen at the same time;

$R^5$ and $R^6$ bond to form a phenyl ring which is optionally substituted;

symbols * and ** represent an optical activity having an axial chirality; and $X^-$ represents an anion.

2. The compound according to claim 1, wherein $R^2$ is hydrogen and $R^{21}$ is halogen, nitro, a $C_{1-8}$ alkyl which is optionally substituted and which is linear, branched, or cyclic, a $C_{2-8}$ alkenyl which is optionally substituted, a $C_{2-8}$ alkynyl which is optionally substituted, a $C_{6-14}$ aryl which is optionally substituted, a $C_{1-8}$ alkoxy which is optionally substituted and which is linear, branched, or cyclic, or a $C_{7-16}$ aralkyl which is optionally substituted.

3. The compound according to claim 1, wherein $R^1$, $R^2$, and $R^{21}$ each independently represents a $C_{1-8}$ alkoxy which is optionally substituted and which is linear, branched, or cyclic.

4. The compound according to claim 1, wherein $R^1$ and $R^{21}$ each independently represents a $C_{1-8}$ alkoxy which is optionally substituted and which is linear, branched, or cyclic, and $R^2$ is hydrogen.

5. The compound according to claim 1, wherein $R^3$ represents a $C_{6-14}$ aryl, which is optionally substituted by halogen, a $C_{1-8}$ alkyl which is optionally substituted by halogen and which is linear, branched, or cyclic, or a $C_{6-14}$ aryl; a $C_{3-8}$ heteroaryl, which is optionally substituted by halogen, a $C_{1-8}$ alkyl which is optionally substituted by halogen and which is linear, branched, or cyclic, or a $C_{6-14}$ aryl; or a $C_{7-16}$ aralkyl, which is optionally substituted by halogen, a $C_{1-8}$ alkyl which is optionally substituted by halogen and which is linear, branched, or cyclic, or a $C_{6-14}$ aryl; and $R^4$ is hydrogen.

6. The compound according to claim 1, wherein $X^-$ is an anion of halogen, OH$^-$, BF$_4^-$, PF$_6^-$, HSO$_4^-$, an anion of $C_{1-6}$ dialkylsulfate which is optionally substituted and which is linear, branched, or cyclic, an anion of $C_{1-6}$ alkylsulfonate which is optionally substituted and which is linear, branched, or cyclic, an anion of $C_{6-14}$ arylsulfonate which is optionally substituted, or an anion of $C_{7-16}$ aralkylsulfonate which is optionally substituted.

* * * * *